(12) United States Patent
Ferlin

(10) Patent No.: US 9,211,117 B2
(45) Date of Patent: Dec. 15, 2015

(54) SURGICAL TREATMENT SYSTEM AND METHOD FOR PERFORMING AN ANASTOMOSIS BETWEEN TWO HOLLOW DUCTS IN A PATIENT, IN PARTICULAR BETWEEN THE BLADDER AND THE URETHRA

(76) Inventor: Arnold Louis Ferlin, Vaux le Penil (FR)

( * ) Notice: Subject to any disclaimer, the term of this patent is extended or adjusted under 35 U.S.C. 154(b) by 480 days.

(21) Appl. No.: 13/821,601

(22) PCT Filed: Sep. 9, 2011

(86) PCT No.: PCT/FR2011/052071
§ 371 (c)(1),
(2), (4) Date: Jun. 5, 2013

(87) PCT Pub. No.: WO2012/032279
PCT Pub. Date: Mar. 15, 2012

(65) Prior Publication Data
US 2013/0267968 A1 Oct. 10, 2013

(30) Foreign Application Priority Data

Sep. 9, 2010 (FR) ...................................... 10 57157

(51) Int. Cl.
*A61B 17/08* (2006.01)
*A61B 17/04* (2006.01)
(Continued)

(52) U.S. Cl.
CPC ......... *A61B 17/0469* (2013.01); *A61B 17/0643* (2013.01); *A61B 17/08* (2013.01);
(Continued)

(58) Field of Classification Search
CPC ........... A61B 17/11; A61B 2017/1107; A61B 17/114; A61B 2017/1132; A61B 17/115; A61B 17/0469; A61B 2017/047; A61B 2017/0472; A61B 17/0482; A61B 17/0643; A61B 17/0644; A61B 17/10; A61B 17/1285; A61B 17/128
See application file for complete search history.

(56) References Cited

U.S. PATENT DOCUMENTS 4,967,949 A * 11/1990 Sandhaus ................ A61F 6/204
227/176.1
5,366,462 A * 11/1994 Kaster ..................... A61B 17/11
128/898

(Continued)

OTHER PUBLICATIONS

International Search Report for PCT/FR2011/052071 dated Feb. 3, 2012.

*Primary Examiner* — Jonathan W Miles
(74) *Attorney, Agent, or Firm* — B. Aaron Schulman, Esq.; Stites & Harbison, PLLC.

(57) ABSTRACT

The treatment system according to the invention comprises: —suture members (20) which are made of a bioresorbable material and each of which has two legs (21, 22) having a respective free end (21A, 22A), the free ends (21A, 22A) being fixedly connectable to each other by having them interact with each other or with an attachment of the suture member in a form-fitting manner, the two legs (21, 22) being elastically deformable at least in part except for said free ends thereof; —an elongate support element (10) which can movably support the suture members and can be inserted into one of the patient's two hollow ducts (2, 3) in the direction of the central longitudinal axis of the support element (10); and —a suture member-biasing mechanism (30) that is movably supported by the support element, is disposed at least in part within the support element, and can move and deform each suture member between a retracted position in which the free ends of the two legs (21, 22) of the suture member can be moved relative to each other as they are both arranged at a radial distance from the axis which is shorter than the outer radius of the support element, and a deployed position in which the free ends of the two legs of the suture member are located outside the support element so as to be fixedly connected to each other as they are both arranged at a radial distance from the axis which is greater than the outer radius of the support element, after having transversely penetrated from the inside to the outside of the respective walls of the patient's two hollow ducts.

30 Claims, 14 Drawing Sheets

(51) Int. Cl.
*A61B 17/064* (2006.01)
*A61B 17/10* (2006.01)
*A61B 17/115* (2006.01)
*A61B 17/11* (2006.01)
*A61B 17/122* (2006.01)
*A61B 17/00* (2006.01)
*A61B 18/00* (2006.01)

(52) U.S. Cl.
CPC .............. *A61B 17/10* (2013.01); *A61B 17/115* (2013.01); *A61B 17/1155* (2013.01); *A61B 17/122* (2013.01); *A61B 2017/00004* (2013.01); *A61B 2017/00274* (2013.01); *A61B 2017/1132* (2013.01); *A61B 2017/1157* (2013.01); *A61B 2018/00547* (2013.01)

(56) References Cited

U.S. PATENT DOCUMENTS

| | | | | |
|---|---|---|---|---|
| 5,425,738 A | * | 6/1995 | Gustafson | A61B 17/1114 606/151 |
| 5,522,823 A | * | 6/1996 | Kuntz | A61B 17/0644 606/142 |
| 5,707,380 A | * | 1/1998 | Hinchliffe | A61B 17/11 606/153 |
| 6,391,035 B1 | * | 5/2002 | Appleby | A61B 17/076 606/142 |
| 6,896,685 B1 | * | 5/2005 | Davenport | A61B 17/0057 606/139 |
| 2002/0019642 A1 | * | 2/2002 | Milliman | A61B 17/11 606/153 |
| 2002/0091398 A1 | * | 7/2002 | Galdonik | A61B 17/11 606/153 |
| 2002/0095164 A1 | * | 7/2002 | Andreas | A61B 17/0057 606/144 |
| 2003/0065345 A1 | * | 4/2003 | Weadock | A61B 17/06166 606/153 |
| 2003/0220657 A1 | * | 11/2003 | Adams | A61B 1/00179 606/139 |
| 2004/0087985 A1 | * | 5/2004 | Loshakove | A61B 17/0057 606/153 |
| 2004/0193185 A1 | | 9/2004 | McBrayer | |
| 2005/0010241 A1 | | 1/2005 | Milliman et al. | |
| 2005/0222492 A1 | | 10/2005 | Adams | |
| 2006/0167477 A1 | * | 7/2006 | Arcia | A61B 17/0469 606/144 |
| 2006/0200177 A1 | * | 9/2006 | Manzo | A61B 17/11 606/153 |
| 2008/0114385 A1 | | 5/2008 | Byrum et al. | |
| 2009/0281560 A1 | | 11/2009 | Wexner et al. | |

* cited by examiner

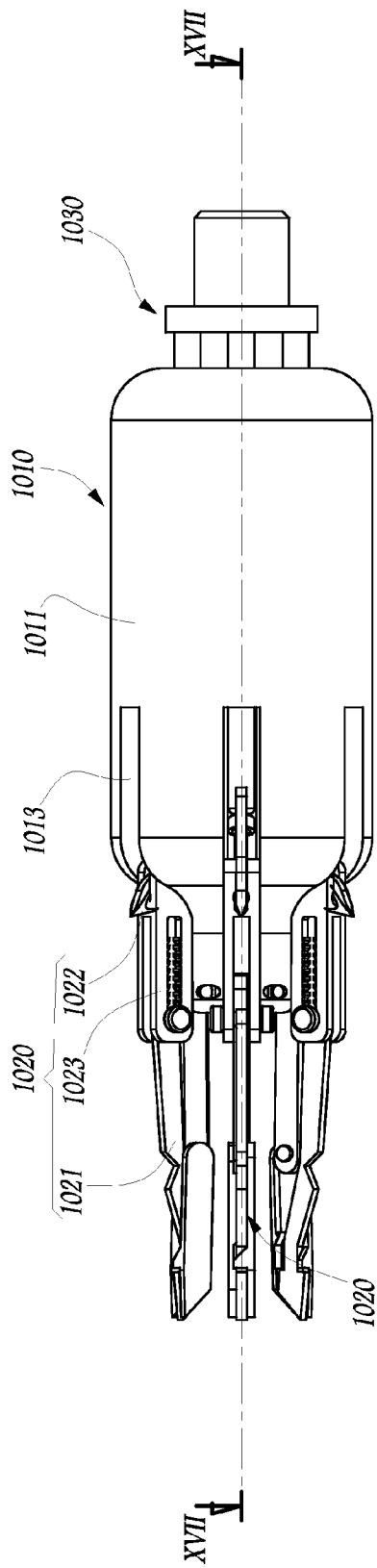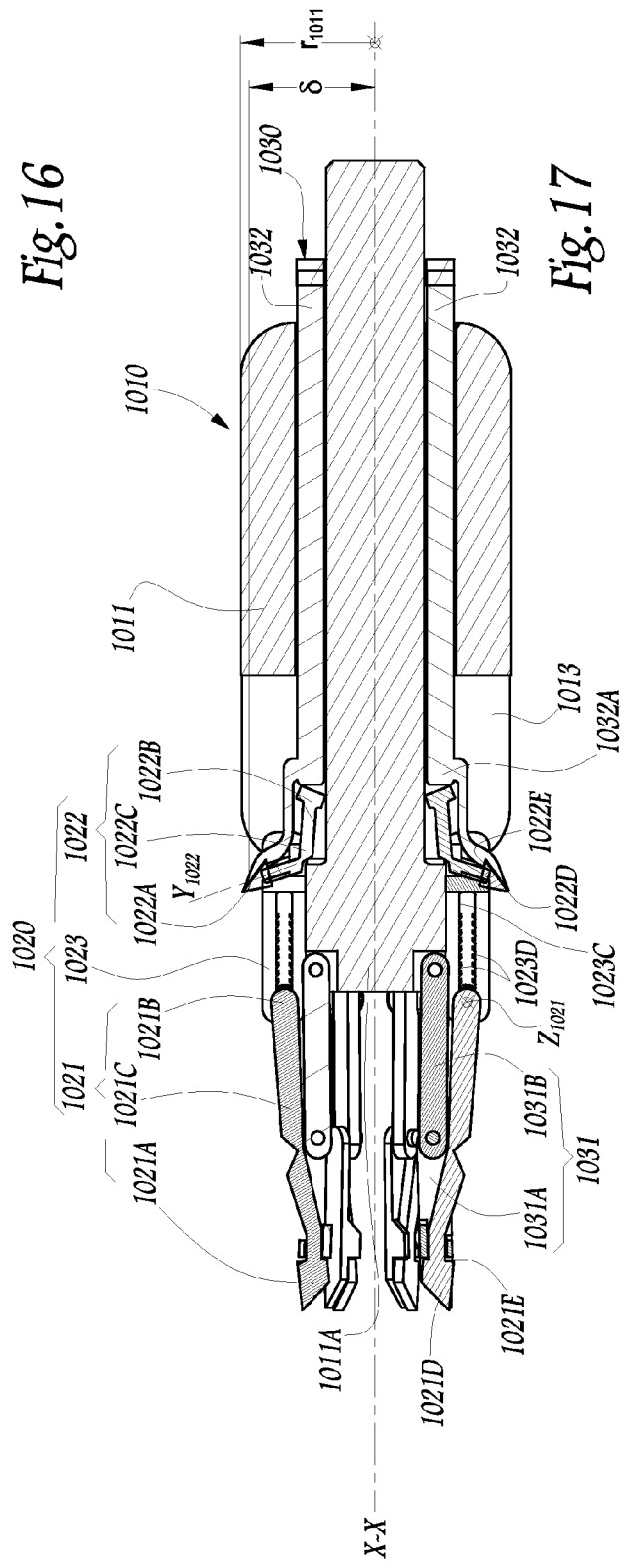

SURGICAL TREATMENT SYSTEM AND METHOD FOR PERFORMING AN ANASTOMOSIS BETWEEN TWO HOLLOW DUCTS IN A PATIENT, IN PARTICULAR BETWEEN THE BLADDER AND THE URETHRA

The present invention relates to a surgical treatment system and method for performing an anastomosis between two hollow ducts of a patient, such as the bladder and urethra of the patient.

The invention therefore relates to the field of surgery, in particular urological, visceral, vascular, etc. surgery. It is for example implemented after a prostatectomy of a patient, so as to surgically reestablish the communication between the neck of the bladder and the terminal orifice of the urethra, opposite the urethral meatus.

In the latter context, traditionally, surgeons perform the anastomosis between the bladder and urethra of a patient using one or more suture threads, which are placed using a needle. This treatment method yields good results, since it makes it possible to join the side of the neck of the bladder and the side of the terminal orifice of the urethra, without having to fold the sides on themselves: it is possible to reestablish a direct contact interface between the respective mucous membranes of the sides, which is favorable to scarring and complete and reliable reestablishment of the communication between the bladder and urethra. However, the implementation of this method requires both a particularly long operating time and great dexterity for surgeons, particularly given that the operating area, behind the pubis, is particularly delicate to access and the sphincter must remain intact throughout the entire operation, in particular avoiding traction, perforation, crushing, etc. thereof.

Another known technique consists of folding each of the sides on itself so as, in a way, to form an inner peripheral flange: after having placed these two flanges alongside one another, they can be sutured to one another by a circular series of staples, placed using a dedicated urethral probe. EP-A-0 282 157 and US-A-2009/0281560 provide examples of this. However, the results of this technique are mixed: each of the sides being folded on itself, the respective mucous membranes are not in contact and cannot scar by "welding" to each other naturally. The necessity will be understood of providing a large number of staples covering most or all of the periphery of the anastomosis area, the staples also made from metal, or more generally non-resorbable, to guarantee that the anastomosis will last. However, the prolonged presence of such metal staples often creates complications in the urological field, typically calculi.

That being said, US-A-2008/114385, which can be considered the closest prior art to the invention claimed here, proposes another approach and discloses a treatment system comprising a plurality of suture members designed to be attached and fastened through the inside of the hollow members to be treated. Each of these suture members is made up of two movable legs, which move from a retracted configuration, in which the free ends of the two legs are arranged at a radial distance from the central axis of a support element that is smaller than the outer radius of said support element, to a deployed configuration, in which the free ends of the legs are driven outside the element, then being located at a radial distance from the aforementioned axis that is larger than the outer radius of the support element, so that said free ends are fastened to the inner surface of the walls of the hollow members to be treated. However, in the aforementioned deployed configuration, the free ends of the legs of the suture members grip the sides of the two joined hollow ducts, folding those sides on themselves, thereby preventing the respective mucous membranes from being in contact with each other. For the same reasons as developed above, the implementation of the system therefore procures mixed results.

The aim of the present invention is to propose a system and a method for performing an anastomosis between two hollow ducts, which are reliable and secure, as well as easy and quick to implement, while obtaining good fastening of the ducts.

To that end, the invention relates to a surgical treatment system for performing an anastomosis, as defined in claim 1.

The invention also relates to a surgical treatment method for performing an anastomosis, as defined in claim 19.

One of the ideas at the base of the invention is to try to use suture members that are both bioresorbable and configured to be implanted in the longitudinal direction of the urethra, each of said suture members overlapping the anastomosis area between two hollow ducts of a patient, such as the urethra and the neck of the bladder. In this way, the respective sides of the two ducts, typically the side of the neck of the bladder and the side of the terminal orifice of the urethra, can be joined, in the tubular extension of one another, forming a direct contact interface between the respective mucous membranes. According to the invention, each of these suture members to that end has two specific legs: the free end of one of said legs is provided to be moved, from the inside to the outside, through the wall of one of the hollow ducts, while the free end of the other leg is provided to be moved from the inside to the outside, through the wall of the other hollow duct, then these two free ends are provided to be fixedly connected to each other in a formfitting manner either with each other, or with an attached part of the suture member, in other words to clip either to one another, or both to the aforementioned attached piece. In practice, across from their aforementioned free end, the two legs are connected by a bridge, which may be flexible and a single piece with the legs, or which may allow guided mobility of one and/or the other of the legs. To place these suture members, the invention provides for using a support element, which may thus be described as a "clip holder": the support element is configured to be placed and immobilized, during the deployment time of the suture elements, inside hollow ducts, then to be released. Furthermore, to deform the suture members suitably in order to fixedly connect the free ends of their legs to each other, the invention provides that the mechanism acting on each of the suture members is inwardly supported by the support element: this mechanism can thus advantageously be controlled through the inside of the ducts, in particular using a probe inserted from a through opening of one of said ducts, said probe also being able to be controlled manually, or partially robotically.

Additional advantageous features of the treatment system according to the invention, considered alone or according to all technically possible combinations, are specified in dependent claims 2 to 18.

The invention will be better understood upon reading the following description, provided solely as an example and done in reference to the appended drawings, in which:

FIG. 16 is an elevation view of part of a second embodiment of a treatment system according to the invention;

FIG. 17 is a cross-section along line XVII-XVII of FIG. 16;

Figure 23:
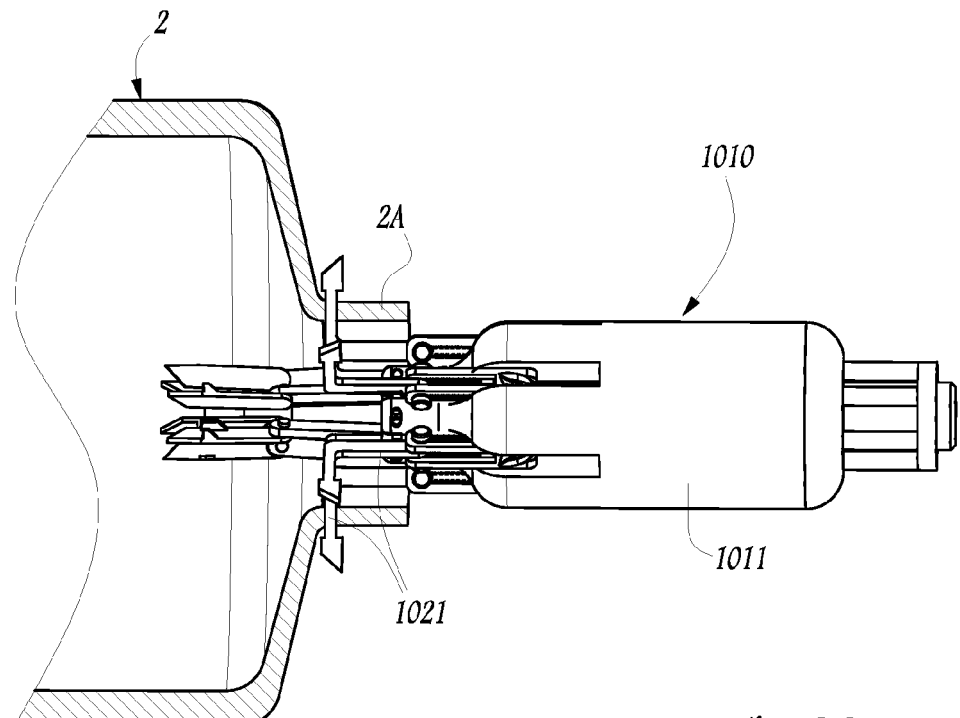

FIGS. 19 to 23 are diagrammatic elevation views, respectively illustrating five successive steps of a use of the system associated with FIG. 16, implemented on the bladder of a patient, shown diagrammatically in longitudinal cross-section; and FIGS. 24 to 28 are diagrammatic elevation views, respectively illustrating five successive steps, following the steps shown in FIG. 23, with a longitudinal cross-section of the bladder and a urethra to be anastomosed to the bladder.

Figure 1:
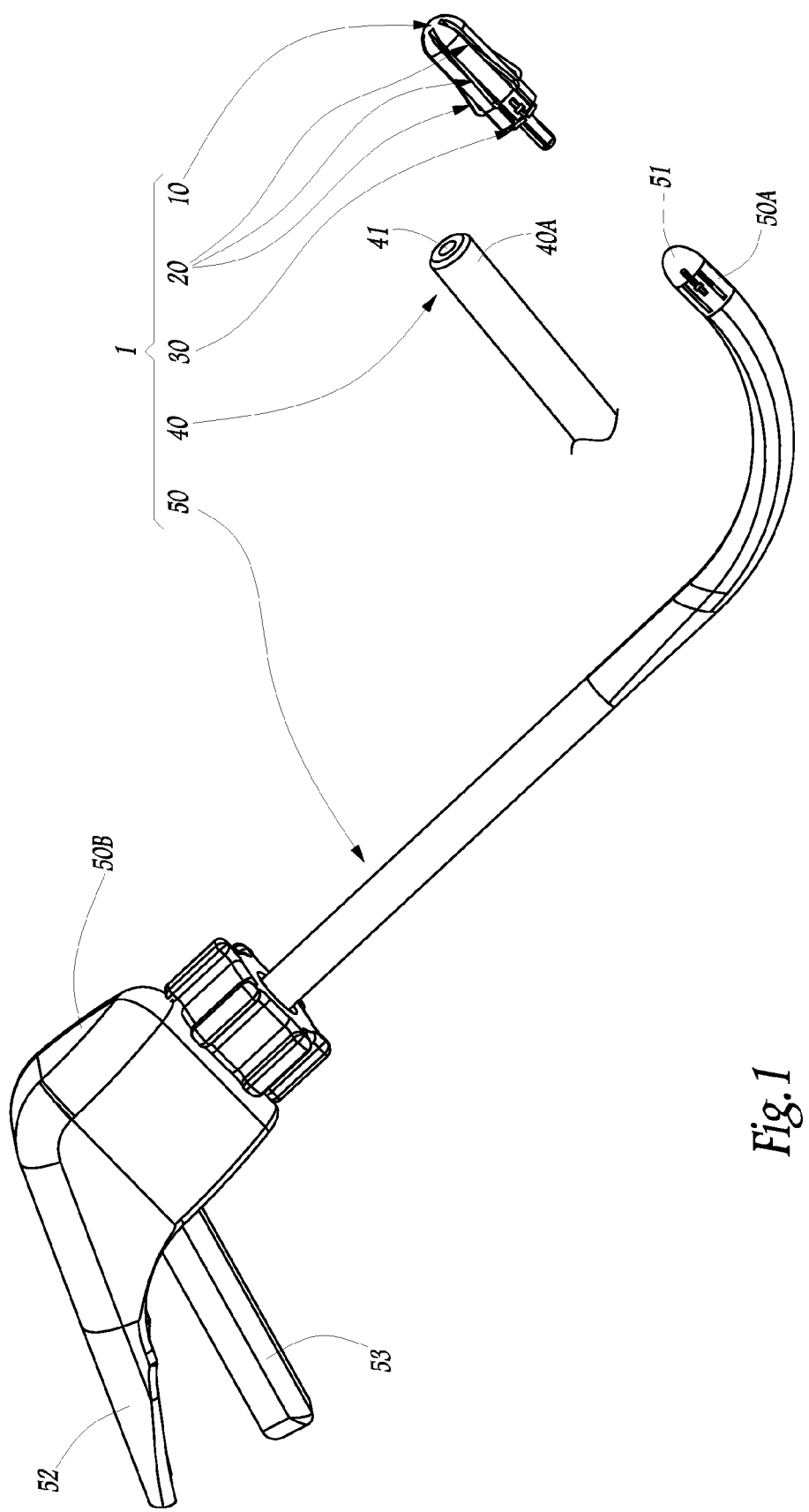
FIG. 1 is a perspective view of a first embodiment of the treatment system according to the invention.
Figure 2:
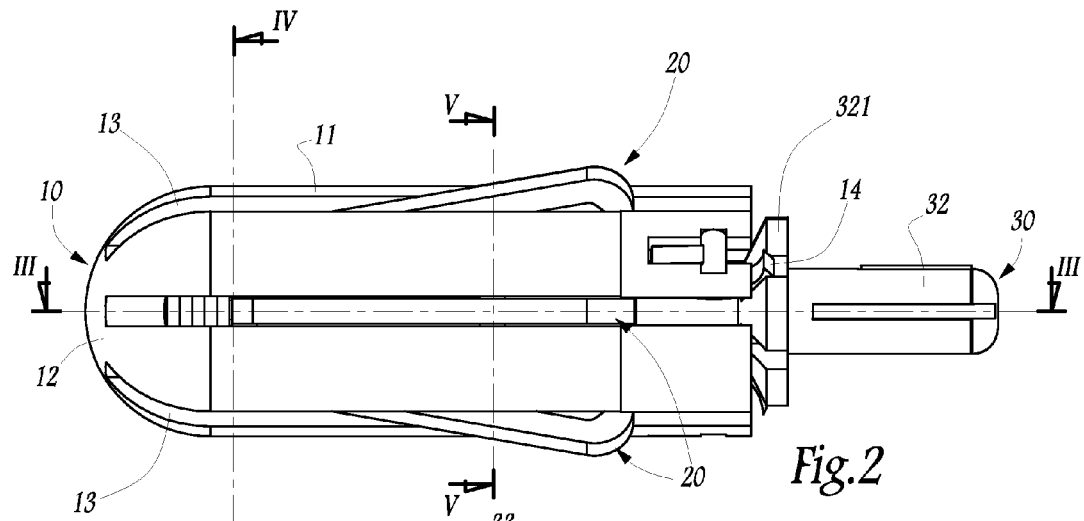
FIG. 2 is an elevation view of part of the system of FIG. 1.

FIG. 1 shows a surgical treatment system 1 for performing an anastomosis between the bladder and urethra of a patient. The system 1 primarily comprises:
an element 10 which, as outlined below, supports one or more suture elements 20 and in which a mechanism 30 is arranged for biasing said suture elements,
an applicator 40 designed to place the element 10 during use of the system 1, and
a urethral probe 50 designed, during use of the system 1, to control the mechanism 30.

The applicator 40 and the probe 50 will be described below, during the detailed presentation of one example of a use of the system 1.

Figure 3:
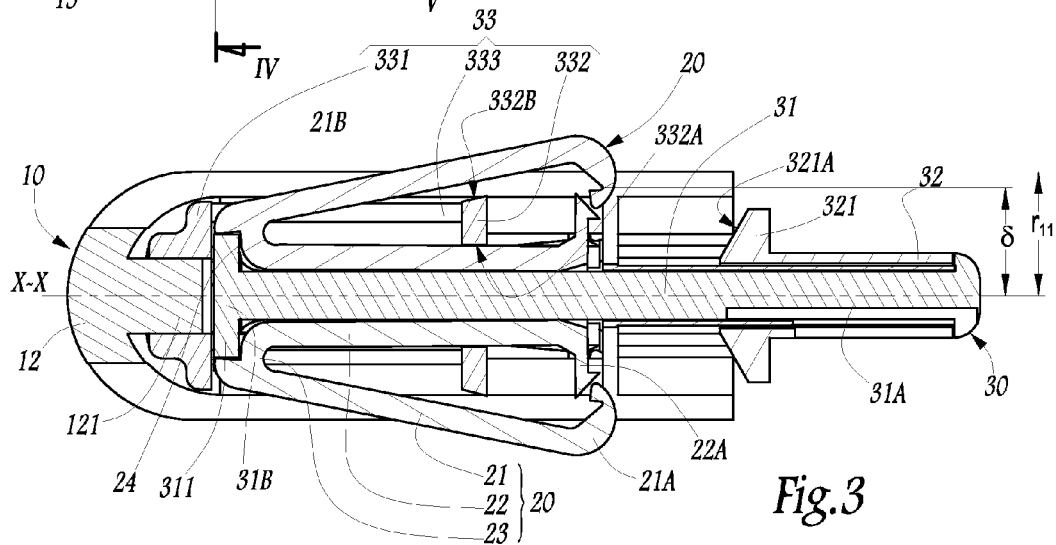
FIGS. 3 to 5 are cross-sections along lines III-III, IV-IV and V-V of FIG. 2, respectively.
Figure 4:
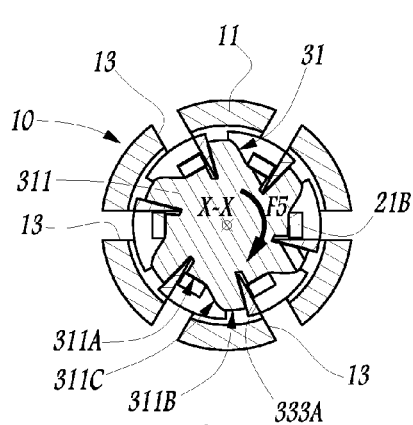
Figure 5:
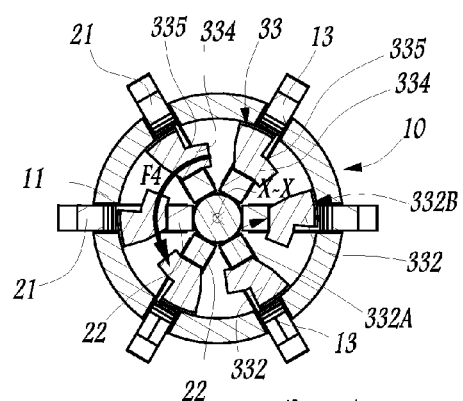

As shown in FIG. 1 and illustrated in more detail in FIGS. 2 to 5, the element 10 has a globally tubular shape, centered on a longitudinal axis X-X. In the example embodiment considered here, the element 10 includes a cylindrical skirt 11 with a circular base centered on the axis X-X. At its distal end, the skirt 11 is closed by a cone-shaped wall 12. At its proximal end, the skirt 11 is axially outwardly open. Furthermore, the inner volume of the skirt 11 communicates with the outside through several through slits 13, which extend lengthwise along the direction of the axis X-X and which are substantially regularly distributed along the periphery of the skirt. In the example embodiment considered in the figures, there are six of these slits 13, as shown in FIGS. 4 and 5. The interest thereof will appear below.

As shown in FIG. 3, each of the suture elements 20 is generally U-shaped. More specifically, each element 20 includes two elongated legs 21 and 22 which, at the distal end thereof, are permanently connected to each other by a transverse bridge 23. This bridge 23 thus connects the legs 21 and 22 in an elastically deformable manner in that, like a flexible hinge connection generally centered on the bridge 23, the legs 21 and 22 can be separated or brought closer to one another, subject to the elastic deformation of the material making up the element 20, without breaking the latter, which thus forms a single-piece part.

Opposite the bridge 23, the legs 21 and 22 respectively have free proximal ends 21A and 22A. As shown in FIG. 3, these free ends 21A and 22A are configured in a substantially complementary way so as to be able to be mechanically engaged with each other and thus fix the legs 21 and 22 to each other at their proximal end. In the example embodiment considered in the figures, the free end 22A of the leg 22 is configured in an angular detent, which protrudes from the rest of the leg 22 toward the leg 21, while the end 21A of the leg 21 is configured as a notch, which is delimited as a hollow in the surface of the end 21A, turned toward the leg 22, and which is dimensioned to receive the end detent of the leg 22 in an adjusted manner. More generally, it will be understood that the free ends 21A and 22A of the legs 21 and 22 have matching raised and/or hollow patterns, able to cooperate to fasten the legs 21 and 22 to each other mechanically when said ends 21A and 22A are sufficiently pressed against each other, in particular in a direction transverse to the longitudinal direction of the legs 21 and 22.

In practice, the suture elements 20 are made from a material that allows flexible deformation thereof, as mentioned above. Furthermore, this material is chosen to be bioresorbable, i.e., a material that can resorb under the physicochemical action of the living tissues in contact with which the material is placed. As a non-limiting example, the material making up the suture elements 20 is a bioresorbable polymer, such as polylactic acid (PLA, PLLA), polyglycolic acid (PGA) or polydioxanone (PDO).

Advantageously, for reasons that will appear below, the leg 21 has, at the distal end thereof, an extension 21B that forms a shoulder 24 with the distal side of the bridge 23.

In the configuration of the suture elements 20 shown in FIGS. 1 to 5, the different suture elements 20, of which there are six here, are essentially arranged inside the element 10, with their legs 21 and 22 that extend lengthwise generally along the direction of the axis X-X. More specifically, as clearly shown in FIGS. 3 and 5, the leg 22 and the bridge 23 of each element 20 are completely arranged inside the free volume of the skirt 11, while the leg 21 is received, with a slight incline, in one of the slits 13, emerging slightly outside the skirt 11, in the proximal portion thereof. During use of the system 1, each suture element 20 can be completely freed from the element 10, by passing through one of the slits 13, generally along a direction radial to the axis X-X. Advantageously, for guiding purposes of the elements 20 during that release, the width of the slits 13, i.e., the spacing between the longitudinal edges of each of said slits, is substantially equal to the thickness of the legs 21 and 22: in other words, in cross-section transverse to the axis X-X, the legs 21 and 22 of each element 20 have a dimension orthoradial to the axis X-X that is substantially equal to the orthoradial spacing of the slits 13, as shown in FIG. 5.

The mechanism 30 includes three primary parts, which are all centered on the axis X-X, while being arranged inside the element 10 or, at the very least, in the axial extension of the inner volume of said element of the proximal side thereof. These three parts are:
a lifting strip 31 which, in the example shown in the figures, is made up of a rectilinear rod centered on the axis X-X, extending substantially over the entire length of the skirt 11 and extending, by its proximal end 31A, to the outside of the element 10,
a push-piece 32 which, in the considered example, is made in the form of a tube arranged coaxially around the proximal end 31A of the lifting strip 31, and
a guide 33 which, in the considered example, on the one hand includes, at its distal end, a tubular nozzle 331 that is arranged coaxially around the complementary nipple 121 protruding from the wall 12 of the element 10 toward the inside of said element both forming a pivot link, and, on the other hand, includes six disc portions 332, which, as shown in FIG. 5, are distributed substantially regularly around the axis X-X, all being situated in a same plane perpendicular to that axis, passing through the middle region of the skirt 11, having specified that each of these portions 332 is rigidly connected to the distal nozzle 331 by a strip 333 that extends parallel to the axis X-X, along the inner surface of the skirt 11.

At its distal end 31B, the lifting strip 31 is provided with an annular protruding head 311 centered on the axis X-X. As shown in FIG. 4, said head 311 has, in cross-section transverse to the axis X-X, an elaborate outer profile, in that that profile is not strictly circular: in this way, said profile has six patterns that repeat identically around the axis X-X one after the other, each pattern including a first segment 311A extending along a direction orthoradial to the axis X-X on the one hand, and a second segment 311B, also extending orthoradial to the axis X-X, but while being radially further from the axis X-X than the segment 311A on the other hand, having specified that the segments 311A and 311B are connected to each other by a cam path 311C.

The lifting strip 31 is mounted in the element 10 both translatably along the axis X-X and rotatably on itself around the axis X-X. In practice, a coupling bearing or a similar guide member is advantageously radially inserted between the lifting strip 31 and the skirt 11 of the element 10.

The push-piece 32 is mounted on the proximal end 31A of the lifting strip 31 translatable along the axis X-X.

Furthermore, the guide 33 is mounted in the element 10 rotating on itself around the axis X-X. In the example embodiment considered in the figures, the guide 33 is thus guided in rotation by the cooperation between its distal nozzle 331 and the nipple 121 of the distal wall 12 of the element 10.

Advantageously, the guide 33 and the lifting strip 31 are rotatably linked to each other, for reasons that will appear below: in the example embodiment, this rotary kinematic connection between the guide 33 and the lifting strip 31 is produced by the mechanical cooperation between the head 311 of the lifting strip and the distal ends 333A of the strips 333, as shown in FIG. 4.

We will now provide a detailed description of one usage example of the system 1, in order to perform an anastomosis between the bladder 2 of a patient, shown in FIGS. 6 to 15, and the urethra 3 of that patient, shown in FIGS. 9 to 15. Typically, the aforementioned patient is treated using the system 1 after having undergone a prostatectomy, typically a complete vesicular prostatectomy or radical prostatectomy.

Initially, it will be considered that the element 10, the suture elements 20 and the mechanism 30 are made available to the surgeon in their relative configuration shown in FIGS. 1 to 5. More specifically, as shown in FIG. 3, each of the six suture elements 20 is arranged in the element 10 such that its leg 22 runs along the lifting strip 31, while being radially inserted between said lifting strip and one of the portions 332 of the guide 33. More specifically, each of the portions 332 of the guide 33 delimits, on the surface thereof turned toward the axis X-X, a radial immobilization surface 332A of the leg 22, as shown in FIG. 5. At the same time, the leg 21 of each suture element 20 extends across from the leg 22, with the insertion between said legs of one of the portions 332. Furthermore, in this initial configuration, the free ends 21A and 22A of the legs 21 and 22 are remote from one another, i.e., more generally, these two free ends do not cooperate with each other. Also in this initial configuration, the head 311 of the lifting strip 31 is housed in the respective shoulders 24 of the suture elements 20, with the distal extension 21B of each leg 21 substantially radially bearing on one of the segments 311A of the transverse profile of said head 311, as shown in FIG. 4.

Figure 6:
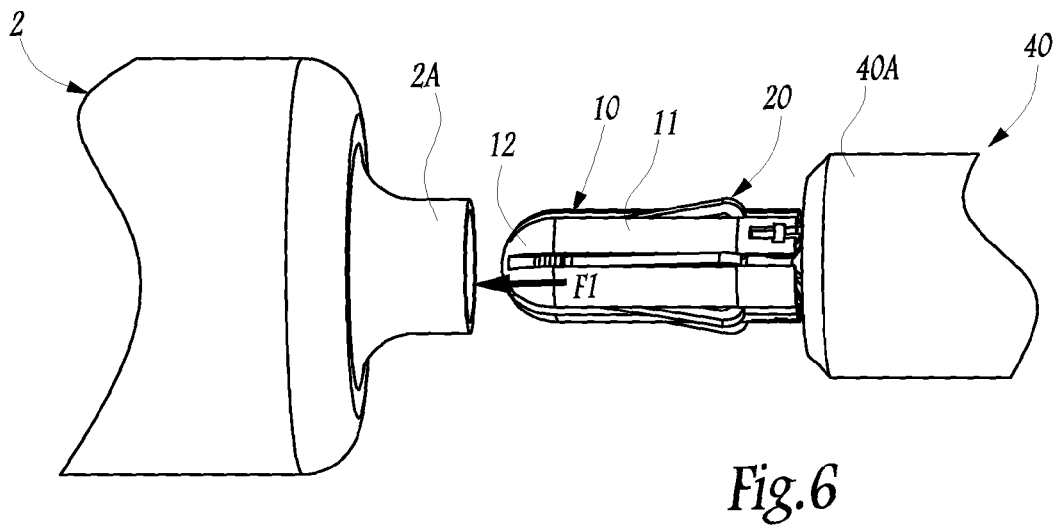
FIGS. 6 and 7 are diagrammatic elevation views, respectively illustrating two successive steps of a use of the system of FIG. 1, associated with the patient's bladder.
Figure 7:
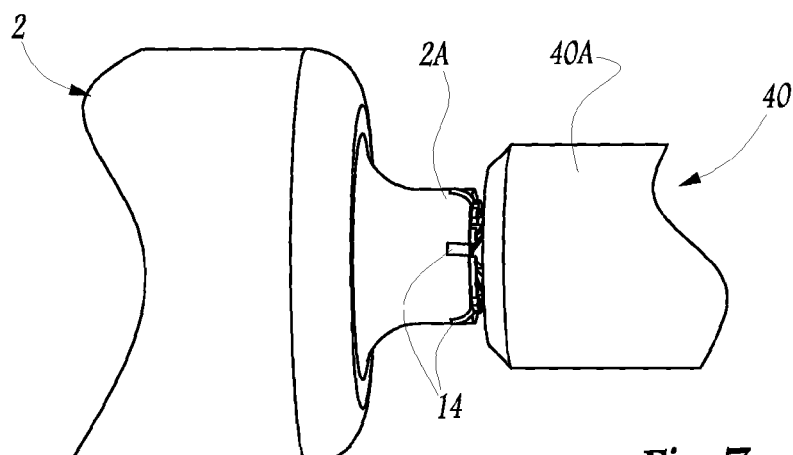

First, the element 10, provided with suture elements 20 and the mechanism 30 arranged according to the initial configuration outlined above, is manipulated using the applicator 40, as shown in FIG. 6. To that end, the proximal end 31A of the lifting strip 31 is engaged and retained in a complementary housing 41 (FIG. 1) delimited at the distal end 40A of said applicator 40. Then, the applicator 40 is manipulated by the surgeon, typically in the context of an endoscopic surgery or an open surgery, to bring the element 10 closer to the bladder 2, until the element 10 is inserted inside the neck 2A of said bladder 2, centering the axis X-X inside said neck 2A and first engaging the distal wall 12 therein, as indicated by the arrow F1 in FIG. 6, the general cone shape of the wall 12 facilitates that placement.

Before this placement of the element 10, the neck 2A of the bladder may need to be surgically reconstructed. In fact, at the sides of the bladder, the neck cannot be ready, inasmuch as it is too wide or not circular, for example. In that case, the surgeon reshapes the neck 2A using a gesture known in itself, either using a thread a needle, or by using the applicator 40 provided with ad hoc means, not shown in the figures of the first embodiment.

In practice, various embodiments, in particular mechanical and/or magnetic, can be considered to mechanically connect the distal end 40A of the applicator 40 to the proximal end 31A of the lifting strip 31, or even, more generally, to a proximal end of the mechanism 30. In all cases, the corresponding coupling means are removable, inasmuch as, through an ad hoc command transmitted by the applicator 40 from its proximal end, the mechanism 30 can be disconnected from the applicator 40, thereby making it possible to release that applicator while leaving the element 10 in place inside the neck 2A of the bladder 2.

Advantageously, the element 10 is provided with mechanical means making it possible to removably immobilize the element 10 with respect to the neck 2A of the bladder 2. As an example, as diagrammatically shown in FIG. 7, such immobilizing means include movable hooks 14: in the initial configuration shown in FIGS. 1 to 5, these hooks 14 are retracted inside the free space of the element 10, in particular the proximal end of that element, then, after positioning of the element 10 in the neck 2A of the bladder 2 using the applicator 40, these hooks 14 are retracted so as to be fastened, in particular by grasping or pinching, to the wall making up the neck 2A of the bladder 2. Advantageously, the command to deploy the hooks 14 is given using the applicator 40.

Of course, embodiments other than hooks 14 can be considered regarding the temporary fastening of the element 10 to the neck 2A of the bladder 2. In particular, according to one alternative not shown, which is less elaborate than the movable hooks 14, the surgeon can use an attached fastening device, such as a surgical thread, for example.

Figure 8:
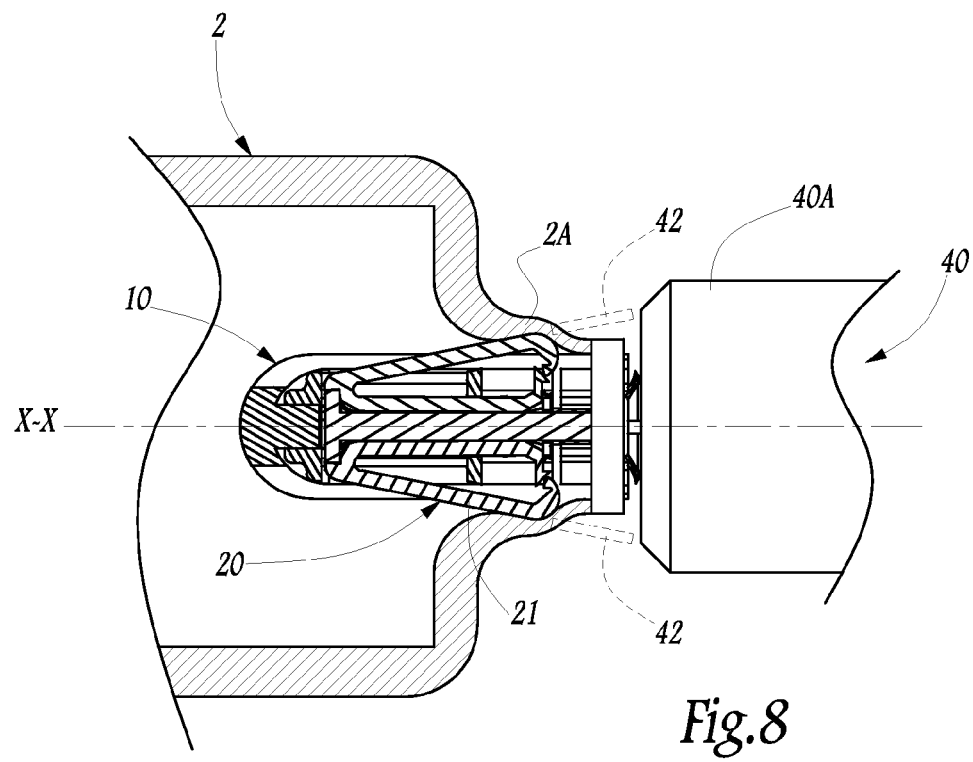
FIG. 8 is a diagrammatic elevation and partial cross-sectional view of the system and the bladder, in the step shown in FIG. 7.

According to one particularly advantageous option, the applicator 40 is provided, at the distal end 40A thereof, with cutting elements 42, only shown in dotted lines in FIG. 8. These cutting elements 42, which are typically small cutting blades or beveled tips, are distributed along the periphery of the distal end 40A of the applicator 40, while advantageously being provided to be deployed protruding from said distal end 42A toward the element 10. It will be noted that the angular positioning of these cutting elements 42 is related to the angular positioning, around the axis X-X, of the suture elements 20: when the element 10 is connected to the applicator 40, the cutting elements 42 are respectively situated axially across from one of the suture elements 20, in other words one of the slits 13. In this way, after having placed the element 10 in the neck 2A of the bladder 2 using the applicator 40 and before releasing that applicator, the cutting elements 42 are used, in particular while being deployed under the action of an ad hoc command transmitted by the applicator 40 from its proximal end, to locally cut the wall making up the neck 2A of the bladder 2, along a direction transverse to the neck and from the outside of that neck. In this way, the six portions of the wall of the neck 2A of the bladder 2, which are respectively situated radially across from the slits 13 and inwardly against which the respective legs 21 of the suture elements 20 lightly bear, are outwardly weakened under the action of the cutting elements 42. If applicable, the action of the cutting elements 42 is such that the aforementioned portions of the wall making up the neck 2A of the bladder 2 are openworked over substantially their entire thickness, which amounts to saying that the cutting elements 42 then come substantially into contact with the legs 21 of the suture elements 20, without, however, damaging those legs.

Figure 9:
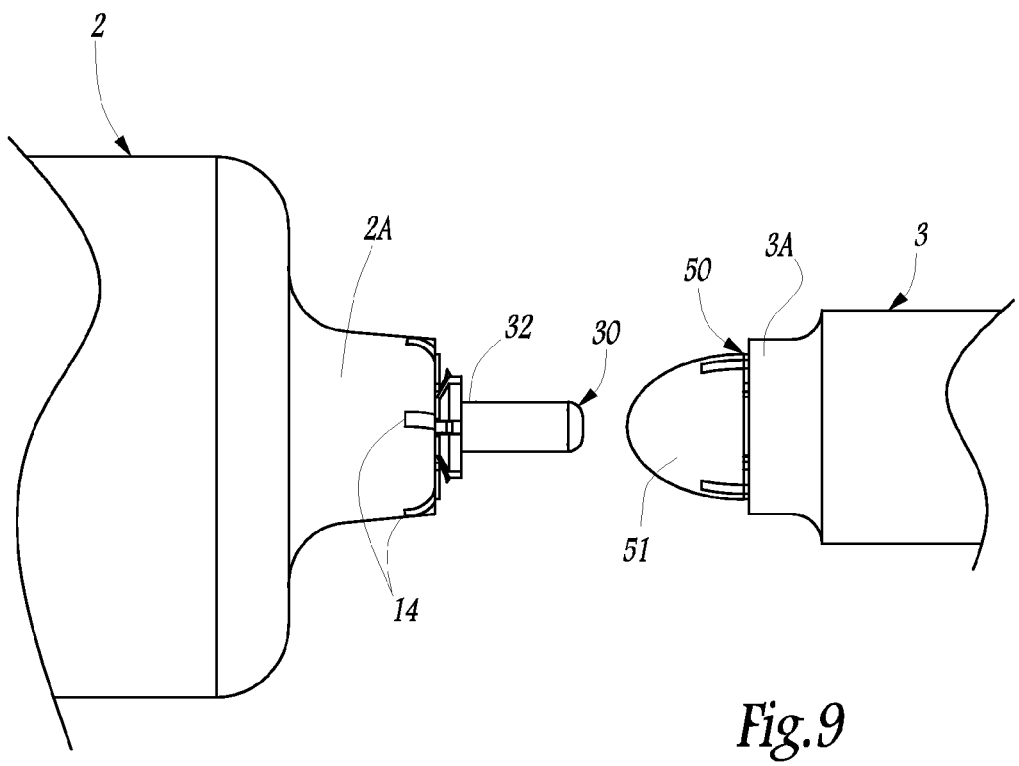
FIG. 9 is a diagrammatic elevation view of the system and the bladder, illustrating a subsequent step of the use of that system, associated with the patient's urethra, to be anastomosed to the bladder.

In a second operating stage, after freeing the applicator 40, the surgeon uses the urethral probe 50, as shown in FIG. 9. In practice, this probe is inserted into the urethra 3 from the meatus thereof, up to an opposite terminal orifice 3A of the urethra, shown in FIG. 9. It will be understood that this terminal orifice 3A results from an earlier resection of the urethra in its membranous area, in particular done in the context of a prostatectomy.

As shown in FIG. 9, the urethral probe 50 is placed in the urethra 3, such that its distal end 50A is situated at the terminal orifice 3A of the urethra 3. To facilitate this placement, the distal end 50A of the probe 50 is advantageously provided with a rounded top 51 which, once the probe 50 is positioned, is released by the surgeon using an additional ad hoc tool.

As one option not shown, before or after releasing the top 51, the distal end 50A of the probe 50 can be removably immobilized in the terminal orifice 3A of the urethra 3, in particular by means that are functionally or even structurally similar to the hooks 14 described above to temporarily immobilize the element 10 in the neck 2A of the bladder 2. If applicable, the top 51 is inwardly provided with means facilitating or participating in said removable fastening.

Figure 10:
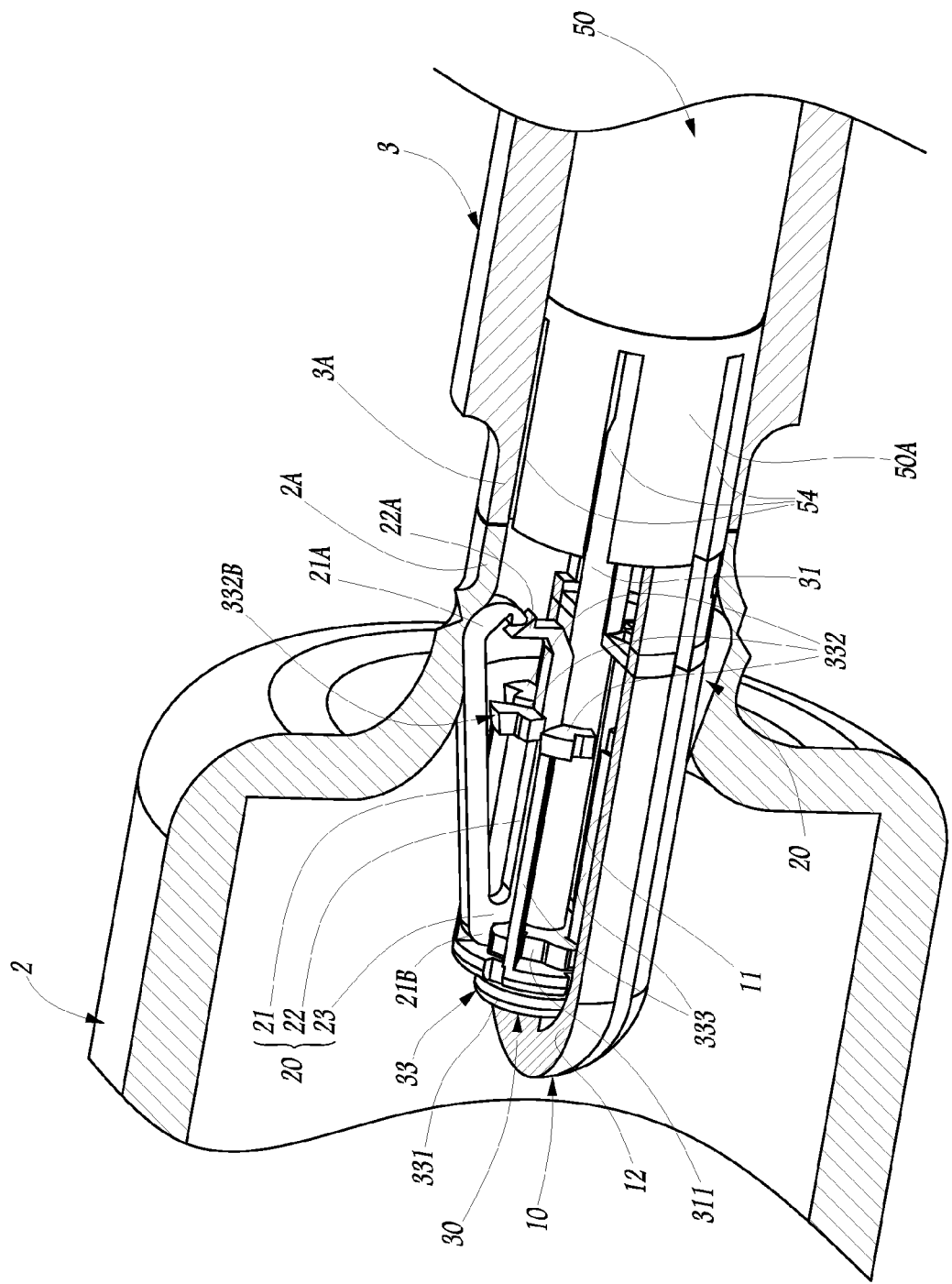
FIG. 10 is a diagrammatic perspective and partial cross-sectional view of the system, the bladder and the urethra, illustrating a step following that shown in FIG. 9.
Figure 11:
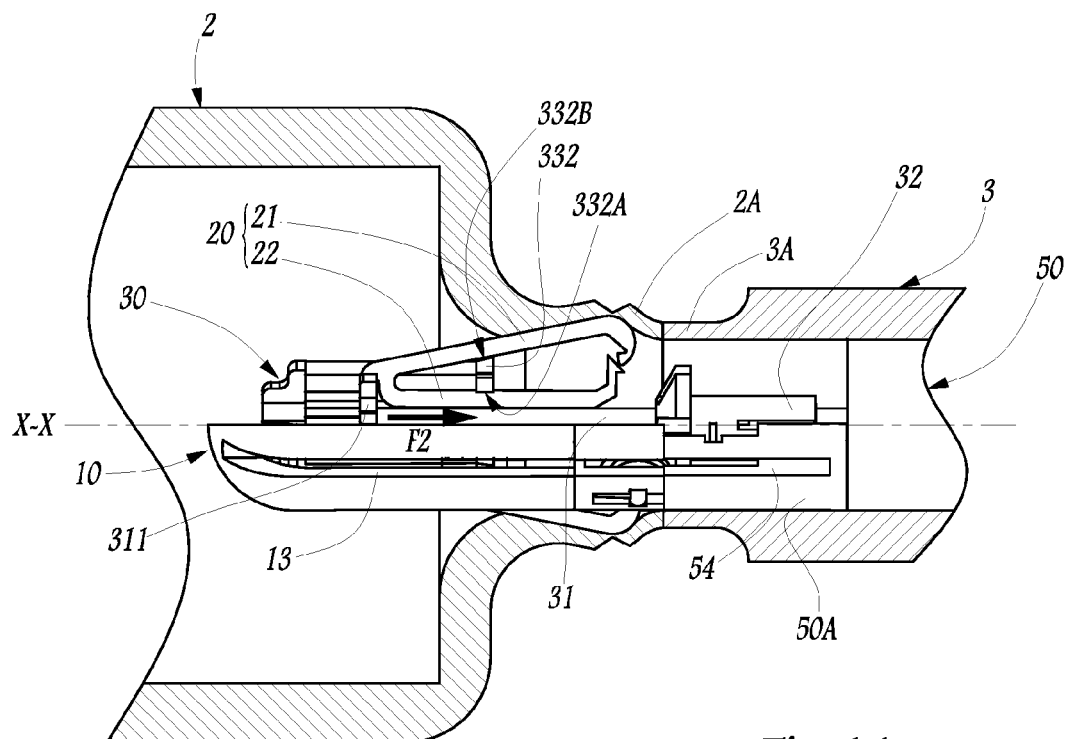
FIG. 11 is a diagrammatic elevation and partial cross-sectional view of the system, the bladder and the urethra, illustrating the same step as that shown in FIG. 10.

In a subsequent surgical stage, illustrated in FIGS. 10 and 11, the surgeon brings the neck 2A of the bladder 2 and the orifice 3A of the urethra 3 closer together. In practice, in particular so as not to damage the sphincter of the urethra 3, it is preferably the bladder 2 that is biased by the surgeon to bring its neck 2A closer to the orifice 3A of the urethra 3. In all cases, the side of the neck of the bladder and the side of the orifice of the urethra are jointly alongside one another, in the tubular extension of one another, as shown in FIGS. 10 and 11. In so doing, the proximal end 31A of the lifting strip 31 is mechanically engaged inside the distal end 50A of the probe 50: in a manner not shown in detail in the figures, this distal end 50A is in fact configured to be assembled in a complementary manner to the proximal end 31A of the lifting strip 31, so as to control the mechanism 30. In other words, inner arrangements of the end 50A of the probe 50 are provided to connect to the mechanism 30 mechanically, so as to allow control of the driving of that mechanism with respect to the element 10. In practice, it will be understood that various embodiments can be considered in this respect as long as the probe 50 is able to transmit command movements to the mechanism 30 from its proximal end 50B, shown in FIG. 1. The corresponding mechanical transmission means, incorporated into the probe, are well known in the field of surgical instruments and, if needed, the reader may refer to the relevant technical literature. Furthermore, in the example embodiment considered in said FIG. 1, the proximal end 50B is made in the form of a manual actuating mechanism, including a fixed handle 52 and a moving strike 53. As one alternative not illustrated, the proximal end 50B of the probe 50 is mechanically connected to an interface that can be connected to a robotic arm, allowing control of the mechanism 30 driven by a computer placed under the supervision of the surgeon, typically in the context of a computer-assisted surgery.

Thus, returning to FIGS. 10 and 11, one can see that, so far, the suture elements 20 and the mechanism 30 are all still in the same initial configuration, shown in FIGS. 1 to 5. This configuration may be described as a retracted configuration regarding the suture elements 20: in fact, as described above, the free ends 21A and 22A of the legs 21 and 22 of each suture element 20 are arranged inside the element 10, and therefore inside the neck 2A of the bladder 2, without cooperating with each other. In other words, in this configuration, the ends 21A and 22A of the legs 21 and 22 are, at most, radially distant from the axis X-X by a value denoted δ in FIG. 3, which is smaller than the outer radius $r_{11}$ of the skirt 11 of the element 10. It will be noted that, for visibility reasons, only two of the six elements 20 are shown in FIGS. 10 and 11, as well as in FIGS. 12 to 15 described below.

Figure 12:
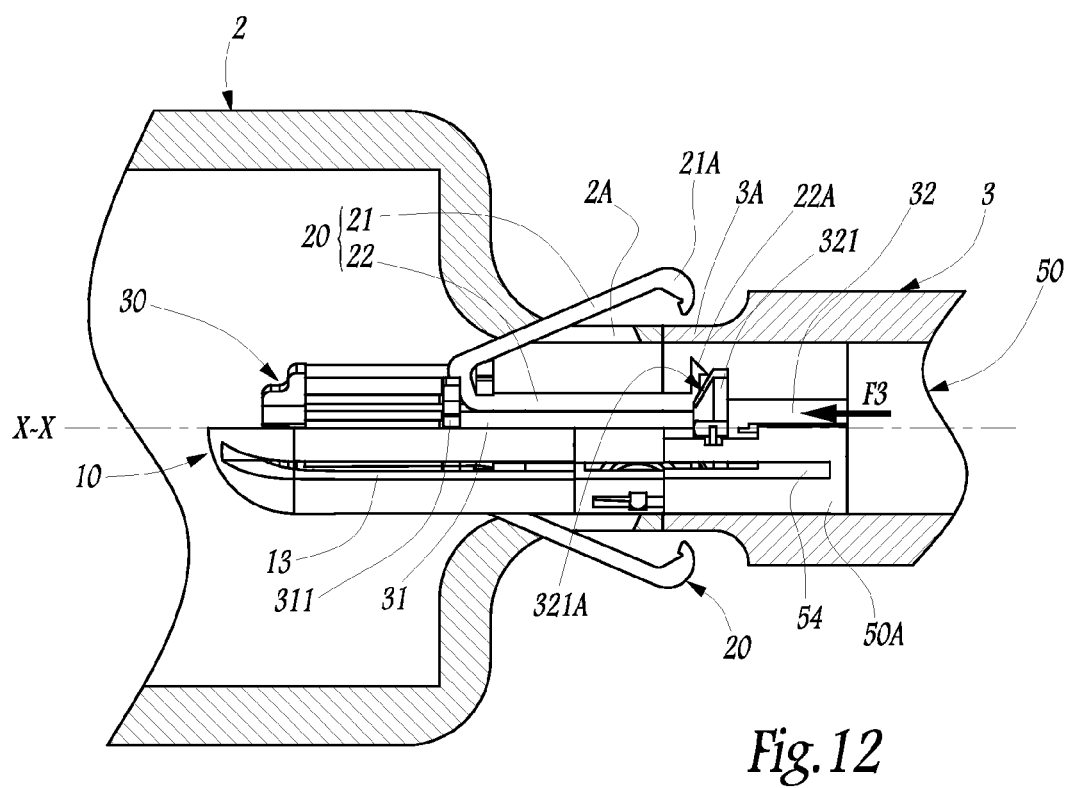
FIGS. 12 to 15 are views similar to FIG. 11, respectively illustrating successive steps of the use of the system.

From this retracted configuration, the surgeon commands the deformation of the suture elements 20 up to a first intermediate configuration, shown in FIG. 12. To that end, the surgeon uses the urethral probe 50 to command the translation of the lifting strip 51 along the axis X-X, oriented toward the surgeon, i.e., oriented opposite the distal wall 12 of the element 10, as indicated by arrow F2 in FIG. 11. By axial bearing of the head 311 against the shoulder 24 of each suture element 20, these suture elements are driven in a corresponding translational movement, as shown by comparing FIGS. 11 and 12, if applicable until causing the legs 22 to bear axially against the push-piece 32 and freely translate that push-piece around the lifting strip 31, as illustrated in FIG. 12. At the same time, due to the axial immobility of the guide 33 inside the element 10, the transverse bridge 23 of each of the suture elements 20 is brought axially closer to the portions 332 of the guide 33: each of these portions 332 then, in a way, forms a relative separating corner between the legs 21 and 22. More specifically, while each of said separating portions 332 radially keeps the leg 22 in place, by radial bearing of its surface 332A against said leg, its radially opposite surface 332B forms a ramp for the leg 21, forcing the separation of that leg with respect to the leg 22 as the suture element is translated under the action of the lifting strip 31. The free end 21A of the leg 21 is thus moved transversely to the wall making up the neck 2A of the bladder 2 and passes all the way through that wall, from the inside out. The passage of each of the legs 21 through the wall of the neck of the bladder is facilitated by the fact that the six portions of that wall thus passed through have previously been weakened by the cutting elements 42, as described above.

Figure 13:
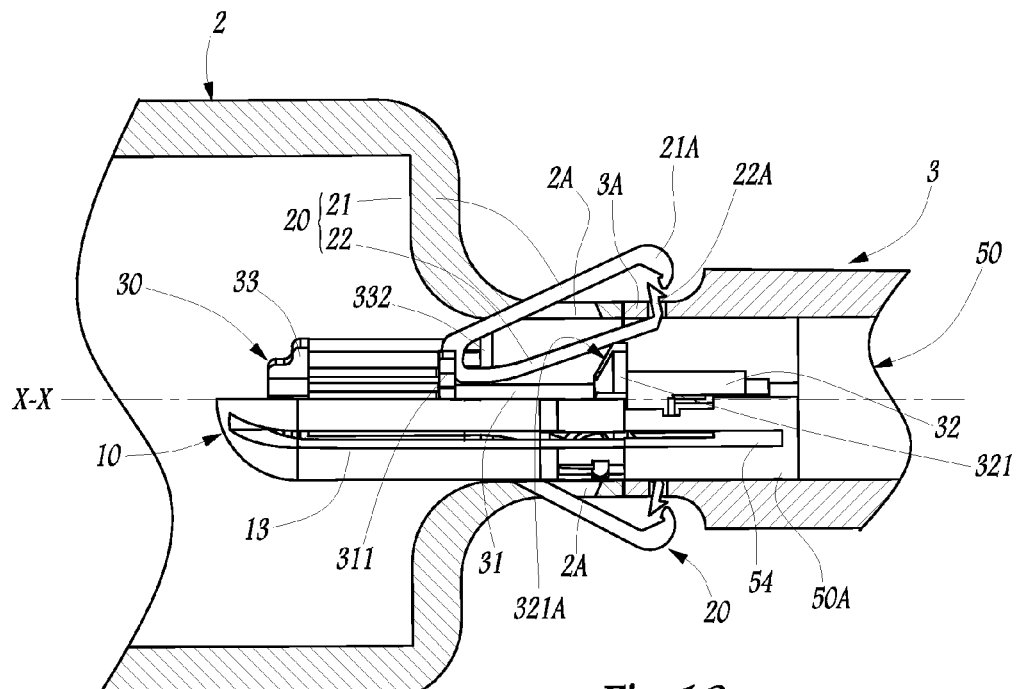

Then, the surgeon uses the urethral probe 50 to command the translation of the push-piece 32 along the axis X-X, toward the wall 12 of the element 10, as indicated by arrow F3 in FIG. 12. The push-piece 32 then tends to drive the leg 22 in a corresponding translational movement. However, given the resistance of the head 311 of the lifting strip 31, then commanded to be immobile along the axis X-X, the leg 22 deforms. More specifically, at its distal end, the push-piece 32 is provided with a head 321 delimiting, on its distal surface, a ramp surface 321A for the legs 22. In the example embodiment considered here, this ramp surface 321A is substantially tapered, centered on the axis X-X and converging toward the wall 12 of the element 10. By ramp effect, this head 321 of the push-piece 32 deforms the leg 22 radially outward, thereby radially bringing its free end 22A closer to the leg 21, causing the wall of the terminal orifice 3A of the urethra 3 to cross that free end 22A, from the inside out, as shown in FIG. 13. The suture elements 20 are then in a second intermediate configuration.

It will be noted that the deformation of the legs 22, in particular the trajectory of the free end 22A, is guided by through slits 54 delimited at the distal end 50A of the probe 50, said slits 54 respectively being provided to extend in the rectilinear extension of one of the slits 13 of the element 10, subject to appropriate angular positioning between the distal end 50A of the probe 50 and the element 10 during the assembly of the probe 50 to the mechanism 30, as shown in FIG. 10.

It will also be noted that the pointed shape, toward the associated leg 21, of the free end 22A of each leg 22 facilitates the passage of that free end through the wall delimiting the orifice 3A of the urethra 3, in fact allowing the transverse perforation of that wall.

Thus, in their second intermediate configuration shown in FIG. 13, the free ends 21A and 22A of their legs 21 and 22 of the suture elements 20 are both positioned outside the element 10, as well as the bladder 2 and the urethra 3, without those free ends cooperating with each other.

Figure 14:
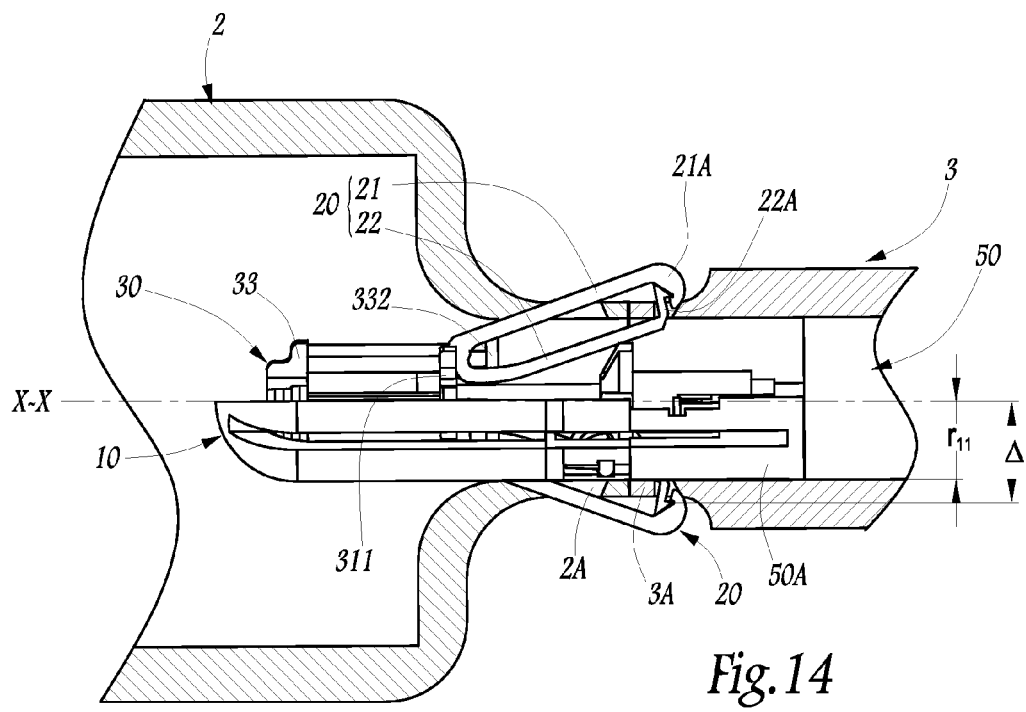
Figure 15:
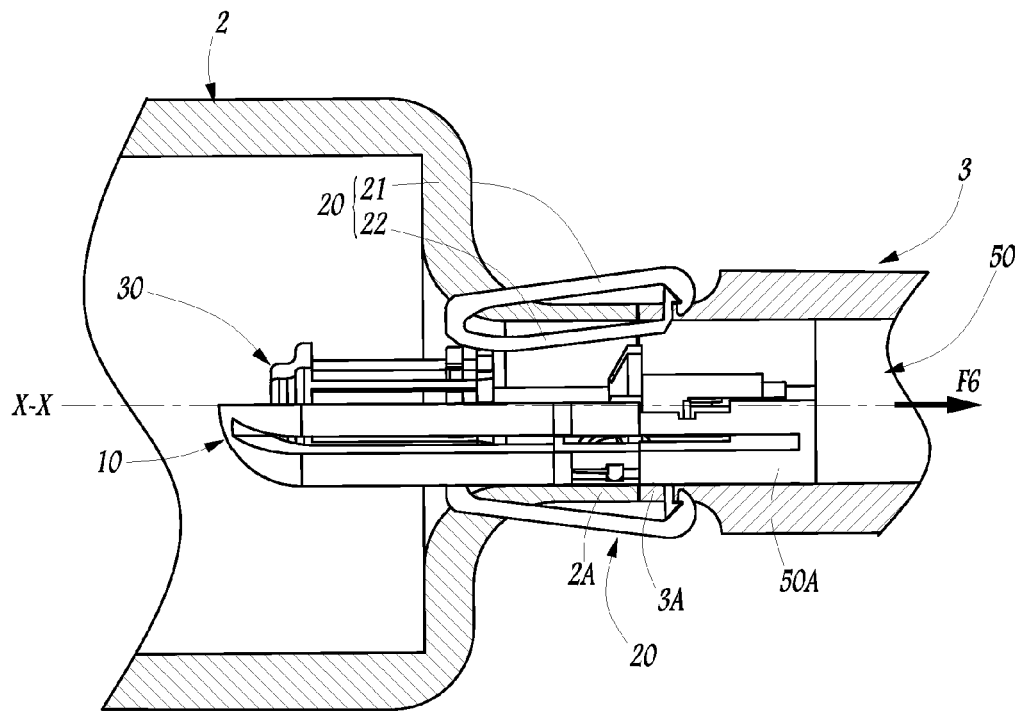

The surgeon will then command the free ends 21A and 22A of the legs 21 and 22 of each suture element 20 to engage with each other, so that said suture elements are in a so-called deployed configuration, shown in FIG. 14. To that end, the surgeon uses the urethral probe 50 to command the rotation of the guide 33 and the lifting strip 31.

Thus, the rotation of the guide 33, which is indicated by arrow F4 in FIG. 5, leads to the release, in a direction orthoradial to the axis X-X, of each of the portions 332 between the legs 21 and 22 of each suture element 20. In other words, by means of this rotation of the guide 33, the ramp surface 332B of each separating portion 332 withdraws orthoradially with respect to the leg 21: by elastic return, this leg 21 then tends to come closer to the leg 22, while engaging its free end 21A with the free end 22A of the leg 22. Advantageously, during this elastic return of the leg 21, the leg 22 is kept radially immobile by the surface 332A of the separating portion 332: to that end, as shown in FIG. 5, each separating portion 332 is provided with a heel 334, which extends the immobilization surface 332A in a direction peripheral to the axis and which, furthermore, is connected to the ramp surface 332B by a hollow shoulder 335 in which the leg 21 is received. The mechanical engagement of the free end 21A with the free end 22A is then straightforward and reliable.

The rotation of the pull tab 31 around the axis X-X, which is indicated by arrow F5 in FIG. 4, leads the distal extension 21B of each leg 21 to follow the cam path 311C of the transverse profile of the head 311 of the lifting strip. In other words, each distal extension 21B is moved, by cam effect, from the segment 311A to the segment 311B of the transverse profile of the head 311, while thus being driven radially toward the outside of the element 10. This displacement through the cam effect biases each leg 21 like a lever, in that the radially outward driving of the distal end of each leg 21 causes a radial tilting toward the inside of its free end 21A, favoring the mechanical engagement of the free end with the free end 22A of the leg 22. Thus, the ends 21A and 22A of the legs 21 and 22 are radially distant from the axis X-X by a value denoted Δ in FIG. 14, which is larger than the outer radius $r_{11}$ of the skirt 11 of the element 10.

The surgeon then needs to finish completely releasing the suture elements 20 with respect to the element 10. To that end, he uses the urethral probe 50 to command the continuation of the rotation of the lifting strip 31 and the guide 33: at the axial level of the head 311, the distal ends 333A of the strips 33 continue the radial release toward the outside of the shoulder 24 of each suture element 20, while, at the axial level of the separating portions 332, the immobilization surfaces 332A withdraw with respect to the legs 22, which, by elastic return with respect to the rest of the suture elements 20, tend to deform radially outwardly. The system 1 is then in the state shown in FIG. 15, with the suture elements 20 in a released configuration with respect to the element 10 and the mechanism 30. The element 10 can then be released, while being discharged through the inside of the urethra 3, by driving with the urethral probe 50, as indicated by arrow F6 in FIG. 15.

The surgical operation is then complete. The suture elements 20 remain in place in their deployed configuration, each overlapping the anastomosis interface made between the neck 2A of the bladder 2 and the terminal orifice 3A of the urethra 3. It will be noted that, advantageously, the surface of the free ends 21A of the legs 21, opposite the associated leg 22, is provided to be rounded, in particular not cutting or perforating, so as not to damage the surrounding biological tissues a posteriori.

Subsequently, the suture elements 20 will gradually be resorbed, after scarring of the anastomosis, the quality of which is remarkable given the direct contact between the mucous membrane of the neck of the bladder and the mucous membrane of the terminal orifice of the urethra.

Various arrangements and alternatives to the system 1 and the method for implementing that system can also be considered. As examples:

Rather than first deforming the leg 21, then the leg 22 of each suture element 20, the mechanism 30 can be arranged to first deform the leg 22, then the leg 21;

Rather than being commanded to rotate jointly, the rotation of the lifting strip 31 and the guide 33 can be commanded independently, in particular depending on the surgeon's wishes;

Optionally, the system 1 includes means for locally weakening the wall of the terminal orifice 3A of the urethra 3 so as to then facilitate the through passage for the free end 22A of the legs 22; in practice, such weakening means are advantageously incorporated into the distal end 50A of the probe and/or into the top 51; in the presence of such weakening means, the pointed shape of these free ends 22A can then be less pronounced, or even omitted;

Optionally, the proximal end of the element 10 and the distal end of the probe 50 can be designed to cooperate with each other directly in a formfitting manner; in this way, the mechanical connection between the element 10 and the probe 50 is reinforced and/or further stressed in the relative positioning; as an example, the skirt 11 is, over a limited portion of its periphery, longitudinally extended to opposite the wall 12, so as to be received in a complementary notch delimited at the distal end of the probe; and/or It will be understood that the legs 21 and 22 described thus far can be globally described as semi-rigid, inasmuch as they associate a flexibility necessary for their deformation with a rigidity necessary for their passage through the walls of the bladder and urethra; in alternatives not shown, one can therefore see that, in some of their portions, one and/or the other of these legs may be more flexible than rigid; more generally, the legs 21 and 22 are provided to be deformable without breaking, for the relative displacement thereof between the retracted and deployed configurations of the suture element 20, having noted that, if necessary, an additional piece can be attached to fixedly connect the free ends of the legs to each other, as will be explained just below relative to another outlined embodiment.

FIGS. 16 and 17 show a second embodiment of a treatment system for performing an anastomosis between the bladder 2 and the urethra 3. Like the system 1 described thus far, the system according to this second embodiment comprises suture members 1020, which, as outlined below, are movably supported by a support element 1010 and are designed to be biased in displacement and deformation by a mechanism 1030 movably supported by the support element 1010. As described below, during the detailed presentation of one example of usage, the system according to this second embodiment also comprises an applicator 1040 and a probe 1050.

As shown in FIGS. 16 and 17, the element 1010 has an elongated shape, centered on a longitudinal axis X-X. In the example embodiment considered here, the element 1010 primarily includes a cylindrical rod 1011 with a circular base, centered on the axis X-X.

Figure 18:
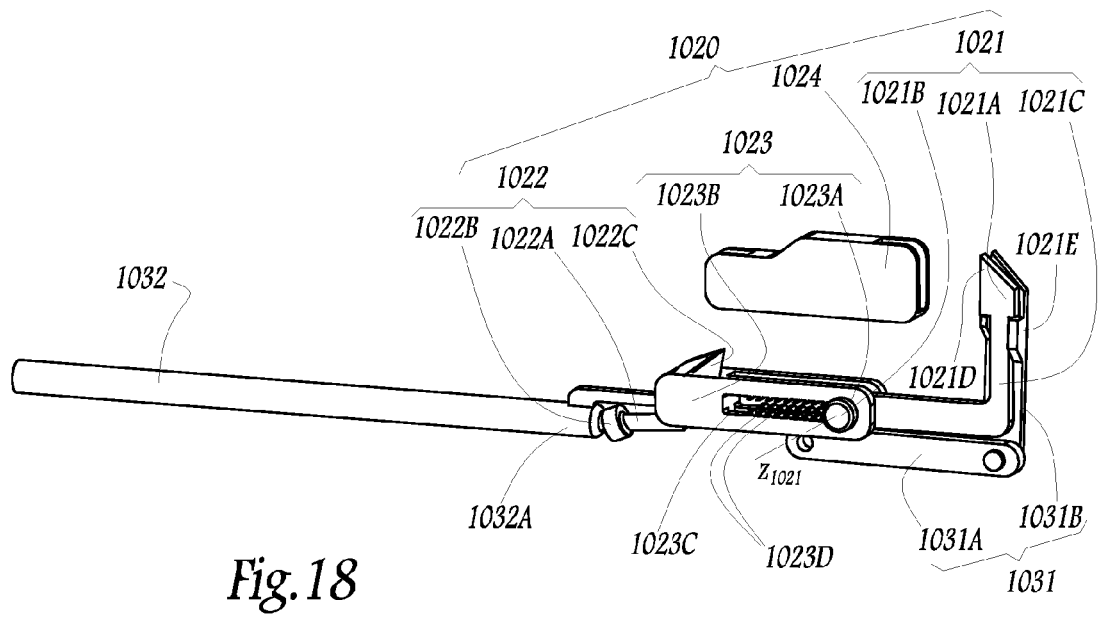
FIG. 18 is a perspective view of only some components shown in FIGS. 16 and 17, in a different configuration.

As shown in FIGS. 17 and 18, each of the suture members 1020 includes four distinct parts, which are assembled together, while allowing mobility between the parts at least in certain configurations of the suture member.

Hereafter, three of the four aforementioned parts will be described in more detail, considering that each suture member 1020 is in an initial configuration relative to the support element 1010, as shown in FIGS. 16 and 17. Thus, among the four aforementioned parts, each member 1020 includes two legs 1021 and 1022 that are movably connected by a bridge 1023 forming a third of the four aforementioned parts. As shown in FIGS. 17 and 18, the bridge 1023 has a substantially rectilinear elongated shape, which extends lengthwise substantially parallel to the axis X-X. Each bridge 1023 is arranged at a choked distal end 1011A of the rod 1011 of the element 1010, while being radially supported in the direction of the axis X-X by the end 1011A of the rod 1011, while being situated, along the periphery of that end 1011A, in the axial extension of the longitudinal slit 1013, and is delimited in the running portion of the rod 1011 while emerging radially on the outside of that running portion, more specifically in the distal end portion of that running portion, which forms a shoulder protruding radially outward with respect to the aforementioned distal end 1011A of the rod 1011. Each bridge 1023 has a distal longitudinal end 1023A relative to which the proximal end 1021B of the corresponding leg 1021 is articulated around a tilting axis $Z_{1021}$ that extends substantially orthoradially to the axis X-X. At its opposite proximal end 1023B, each bridge 1023 has a through hole or groove, centered on an axis $Y_{1022}$ transverse to the axis X-X: as shown in FIG. 17, the running portion 1022C of the leg 1022 is slidingly received in the hole delimited by the proximal end 1023B of the bridge 1023, while being oriented along the axis $Y_{1022}$.

Advantageously, for reasons that will appear later, each bridge 1023 inwardly delimits, along the length of its running portion, a substantially rectilinear slit 1023C, which connects the ends 1023A and 1023B, and in the distal end of which the proximal end 1021B of the leg 1021 is arranged, articulated around the tilting axis $Z_{1021}$. In this way, the proximal end 1021B of the leg 1021 can be brought closer, along the direction of the axis X-X, to the proximal end 1023B of the bridge 1023, and under operating conditions that will be outlined later, having noted that the opposite return of the end 1021B of the leg 1021 is made impossible by the backstop teeth 1023B with which the slit 1023C is inwardly provided.

Opposite its free end 1021B, each leg 1021 has a free end 1021A provided with a perforating tip 1021D. Advantageously, for reasons that will appear later, this tip 1021D has, in its connecting area with the running portion 1021C of the leg 1021, a larger transverse section than that of the running portion 1021C, so as thus to form a transitional shoulder 1021E.

The leg 1022 has a proximal end 1022B and a free end 1022A opposite one another and connected by the running portion 1022C of said leg. Said free end 1022A has arrangements similar to those of the free end 1021A of the leg 1021, i.e., a tip 1022D and a transition shoulder 1022E with the running portion 1022C.

In the initial configuration of FIGS. 16 and 17, the running portion 1021C of each leg 1021 extends lengthwise globally along the direction of the axis X-X, which means that that running portion 1021C extends substantially in the rectilinear extension of the connecting bridge 1023. The running portion 1022C of the leg 1022 is bent, the proximal segment of said running portion 1022C extending lengthwise substantially parallel to the axis X-X, occupying the radial bottom of one of the slits 1013, while the distal segment of the running portion 1022C is received in the hole or the groove, delimited at the proximal end 1023B of the connecting bridge 1023.

Similarly to what was described for the first embodiment, the initial configuration, described thus far, of the suture members 1020 can be described as a retracted configuration with respect to the element 1010, inasmuch as, in that configuration, the free end 1021A and 1022A of the legs 1021 and 1022 of each member 1020 are, at most, radially distant from the axis X-X by a value δ that is smaller than the maximum outer radius $r_{1011}$ of the rod 1011 of the element 1010, as indicated in FIG. 17. As before for the first embodiment, this arrangement of the suture members 1020 makes it possible, as explained below, to insert the element 1010 inside an inlet orifice of the bladder 2, without interfering with the edge of that inlet orifice. Of course, the tissues of the bladder 2 may be slightly stretched if the diameter of the neck of the bladder at rest is too small.

The mechanism 1030 is designed, similarly to the mechanism described for the first embodiment, to displace and deform the suture members 1020 to switch them from their initial retracted configuration of FIGS. 16 and 17 to a final deployed configuration, described below. In the example embodiment considered here, this mechanism 1030 comprises various components that will be described below in the context of a detailed example of the use of the corresponding system, so as to perform an anastomosis between the bladder 2, shown in FIGS. 19 to 28, and the urethra 3, shown in FIGS. 24 to 28.

Figure 19:
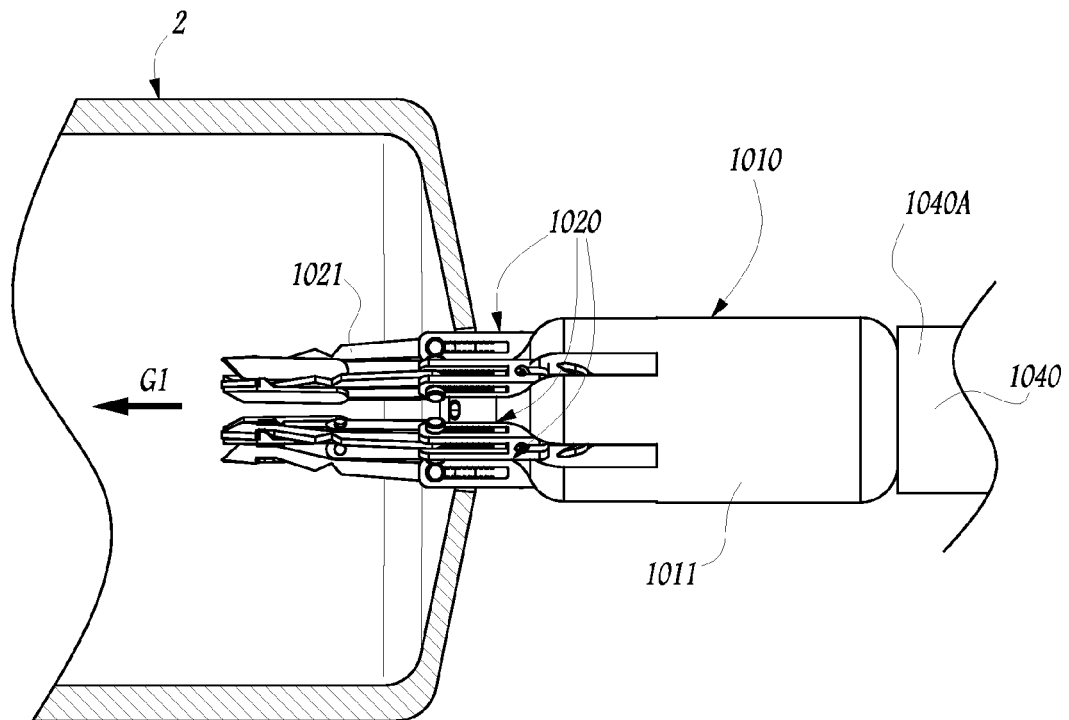

Initially, it is considered that the element 1010, the suture members 1020 and the mechanism 1030 are made available to the surgeon in the relative configuration illustrated in FIGS. 16 and 17. The element 1010 is then manipulated using the applicator 1040, as shown in FIG. 19: the element 1010 is brought closer to the bladder 2, until at least the distal end 1011A of its rod 1011 is inserted inside an inlet orifice 2B of the bladder 2, centering the axis X-X inside that inlet orifice and first engaging the legs 1021 of the suture members 1020 therein, as indicated by arrow G1 in FIG. 19.

By means of a command described later, the mechanism 1030 then biases the legs 1021 of the suture members 1020 to move each of those legs 1020 from its substantially rectilinear initial configuration of FIG. 19 to a deformed U-shaped configuration shown in FIG. 21, going through an L-shaped intermediate configuration shown in FIG. 20. To that end, the mechanism 1030 comprises, for each of the legs 1021, an articulated arm 1031 that comprises, along its length:

- a first rectilinear segment 1031A, one longitudinal end of which is articulated on the distal end 1011A of the rod 1011, and
- a second rectilinear segment 1031B whereof the end turned toward the first segment 1031A is articulated on the end thereof, opposite that articulated on the rod 1011.

Figure 20:
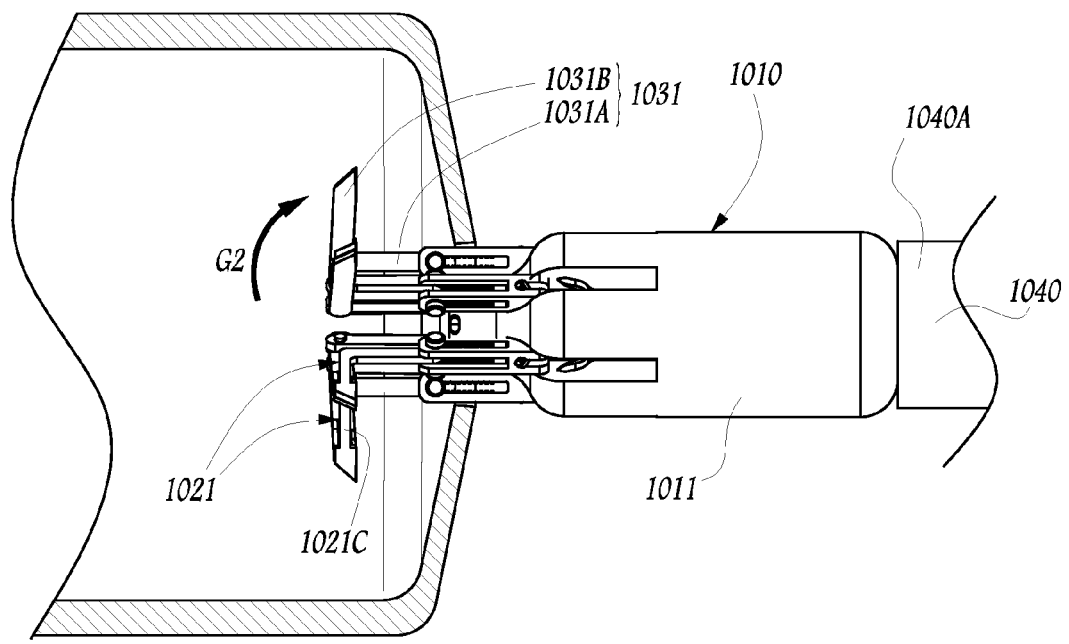
Figure 21:
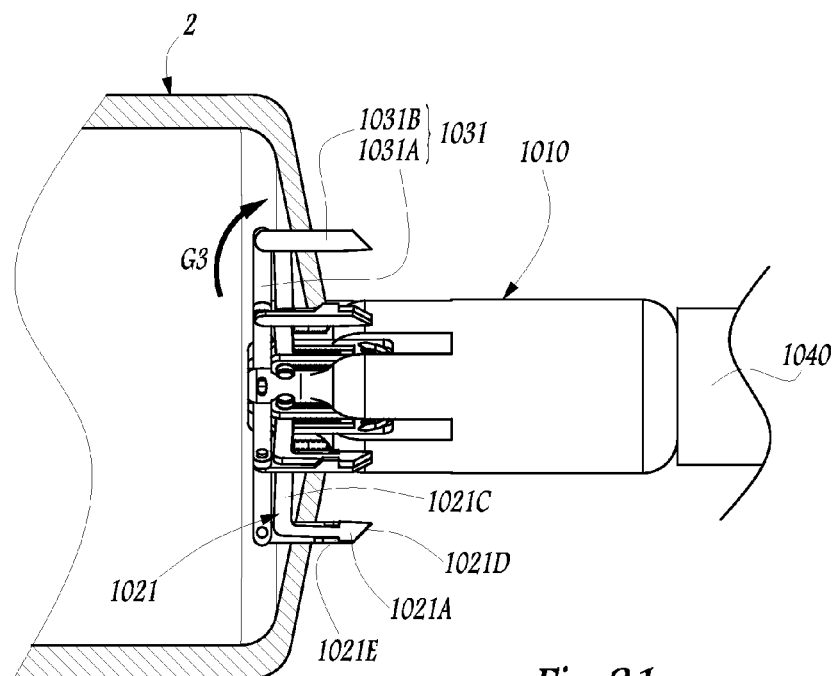
Figure 22:
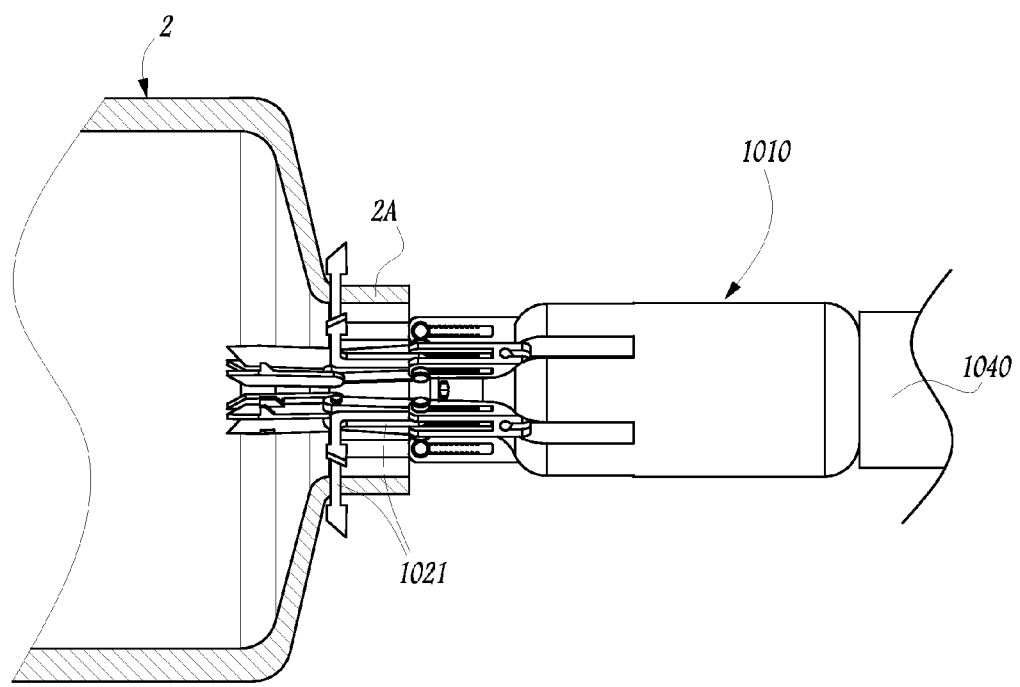

As shown in FIGS. 17 and 18, the running portion 1021C of each leg 1021 runs along the segments 1031A and 1031B, while being removably connected to these segments such that, by tilting the segment 1031B by 90° relative to the segment 1031A, indicated by arrow G2 in FIG. 20, the running portion 1021C of each leg 1021 forms an L, as in FIG. 20, then, by tilting the segment 1031A at 90° at the distal end 1011A of the rod 1011, indicated by arrow G3 in FIG. 21, the running portion 1021C is configured in a U shape, as shown in FIG. 21. In practice, in light of the presence of the wall of the bladder 2, delimiting the inlet orifice 2B, the free end 1021A of each leg 1021 pass all the way through the aforementioned wall of the bladder 2, transversely from the inside out, when the leg goes from its L shape to its U shape. The transverse perforation of the aforementioned wall of the bladder 2 is made by the tip 1021D of each free end 1021A and/or by the free end, for example beveled to that end, of the segment 1031B. In all cases, once the tip 1021D is outside the bladder, the shoulder 1021E then precludes the tip 1021D from passing back through the wall of the bladder in the opposite direction. Thus, it will be understood that the arms 1021 are designed to guide and stress the legs 1021 of the suture members 1020 to move the suture members between the initial configuration of FIG. 19 and the intermediate configuration of FIG. 21.

In practice, the arms 1031 are moved relative to the element 1010 under the action of ad hoc control means, by means of the applicator 1040. As an example, such control means comprise or consist of mechanical transmission cables, which extend from the distal end 1040A of the applicator 1040 to the inside of the rod 1011 of the element 1010, until they rejoin the segments 1031A and 1031B of each of the arms 1031. More generally, it is provided that the distal end 1040A of the applicator 1040 is configured to cooperate with, and thereby control part of the mechanism 1030, kinematically connected to the arms 1031.

Of course, it will also be understood that, for the legs 1021 to go from the rectilinear configuration of FIGS. 16 and 17 to their deformed U-shaped configuration of FIG. 21, the running portion 1021C is elastically deformable or, more generally, deformable without breaking. In practice, the examples of bioresorbable materials previously provided for the first embodiment can be considered to produce the running portion 1021C of the legs 1021, or, more generally, to produce all of the legs 1021. More generally, inasmuch as the arms 1031 support and guide the legs 1021 in their movement all throughout their implementation, it will be understood that such legs 1021 may have a certain rigidity as well as a certain flexibility, as long as they deform sufficiently during use without breaking.

According to one particularly advantageous option, the legs 1021 and the mechanism 1030 are designed to make it possible to tubularize the wall of the bladder 2, through which the ends 1021A of the legs 1021 have passed. This is for example the case with the embodiment of the driving arms 1031: in fact, from the configuration of FIG. 21 in which each suture member is generally U-shaped, dedicated gradual switching kinematics for each articulated arm 1031 allow the shoulder 1021E of the free end 1021A of each leg 1021 to drive the aforementioned wall of the bladder 2 until it has a globally tubular shape, as in FIG. 22, thereby easily and effectively reconstructing a neck 2A for the bladder 2. Concomitantly, after release between the free end 1021A of each leg 1021 and the second segment 1031B of the corresponding arm 1031, the latter is returned to its initial position, while the running portion 1021C of the leg 1021 keeps its L shape. Again, it will be understood that the relative switches between the segments 1031A and 1031B of each arm 1031 are controlled by ad hoc means, by means of the applicator 1040.

Figure 24:
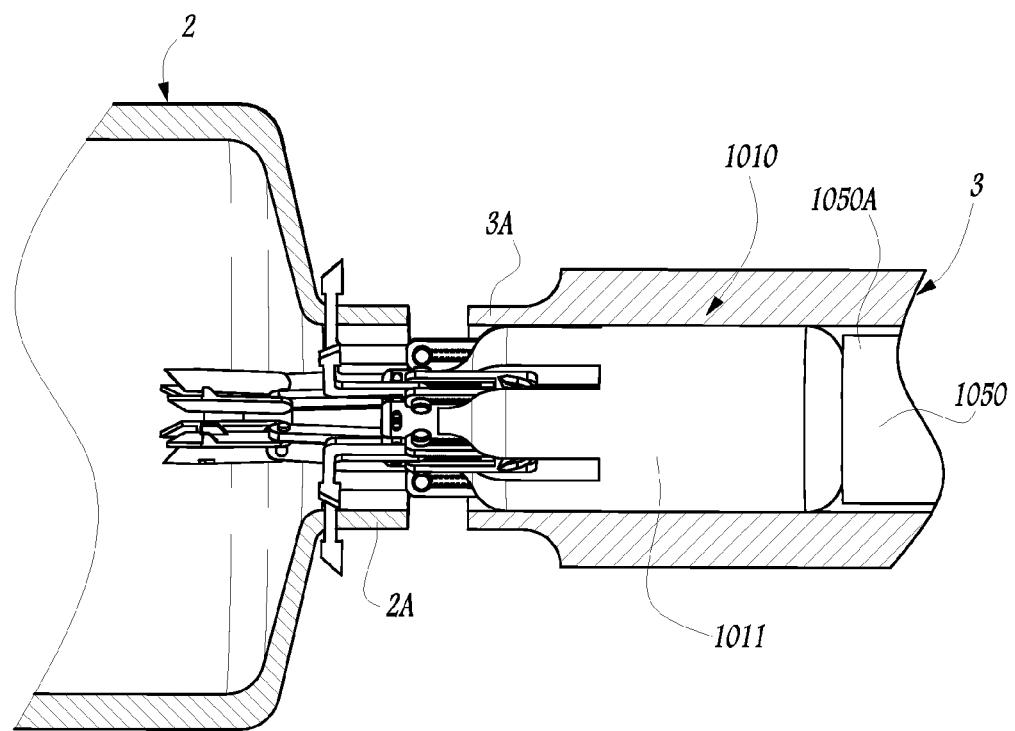

In a subsequent operating stage, the applicator 1040 is released, as shown in FIG. 23, then the surgeon uses the urethral probe 1050, as shown in FIG. 24, in particular in the case of a radical prostatectomy. As described in detail above relative to the first embodiment, this probe 1050 is inserted into the urethra 3 from the meatus thereof, as far as the opposite terminal orifice 3A of the urethra, visible in FIG. 24.

Figure 25:
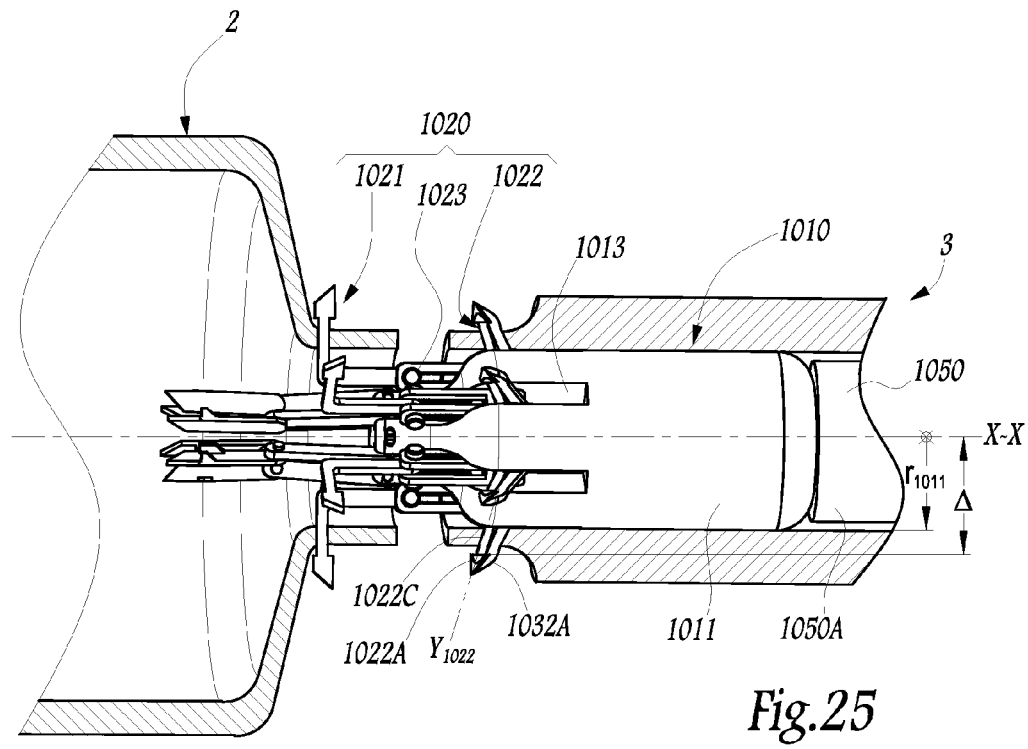

The surgeon then uses the urethral probe 1050 to command the displacement and deformation of the legs 1022 of the suture members 1020: each of said legs 1022 goes from its initial configuration of FIGS. 16 and 17 to a deployed configuration shown in FIG. 25. In practice, in the embodiment considered here, each leg 1022 is biased in displacement and deformation by a dedicated push-piece 1032, two of these push-pieces being shown in cross-section in FIG. 17, the movements of which are controlled by the probe 1050, by cooperation between the proximal end of the push-piece and the distal end 1050A of the probe. Thus, each of said push-pieces 1032 is translatably mounted along the direction of the axis X-X, while being slidingly received in complementary passages delimited, along the direction of the axis X-X of the rod 1011, through each of the aforementioned through passages, on the distal side, in one of the slits 1013, subject to its translation along the direction of the axis X-X, in the distal direction, under the control action of the probe 1050, each push-piece 1032 drives, by its free end 1032A, the proximal end 1022B of the corresponding leg 1022 in a corresponding translational movement. However, in light of the resistance of the corresponding bridge 1023, then commanded to be immobile along the direction of the axis X-X, the leg 1022 deforms by ramp effect. More specifically, the running portion 1022C thereof gradually passes through the hole or the groove, delimited in the proximal end 1023B of the bridge 1023, thereby forcing the longitudinal segment of that running portion 1022C, emerging from the end 1023B, to translate along the direction of the axis $Y_{1022}$, moving away from the rod 1011. Thus, the free end 1022A of each leg 1022 translates along the corresponding axis $Y_{1022}$, moving away from the element 1010. As shown by comparing FIGS. 23 and 24, this free end 1022A thus goes from the inside to the outside of the wall delimiting the orifice 3A of the urethra 3, the transverse perforation of that wall being done by the corresponding tip 1022D and/or by the free end 1032A, for example extended and ending with a cutting edge, of the corresponding push-piece 1032, while the corresponding shoulder 1022E then prevents the tip 1022D from passing back through the aforementioned wall in the opposite direction. Of course, based on similar considerations developed above for the running portion 1021C of the legs 1021, it will be understood that the running portion 1022C of the legs 1022 is also made from a deformable material, so as to bear its gradual bending through the end 1023B of the bridge 1023 without breaking. More generally, inasmuch as the cooperation between the element 1010, the push-pieces 1032 and the bridges 1023 immobilized on the element 1010 supports and guides the legs 1022 in their displacement all throughout their implementation, it will be understood that these legs 1022 may have a certain rigidity as well as a certain flexibility, as long as they deform sufficiently during use, without breaking.

Figure 26:
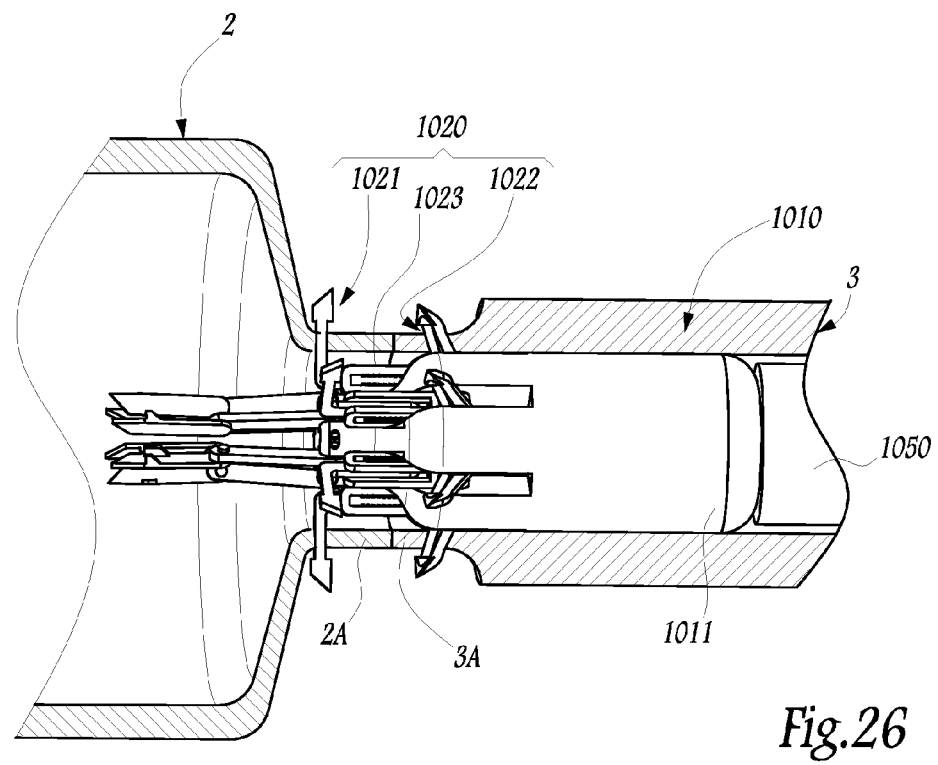

Thus, at this stage of the operation, it will be noted that the ends 1021A and 1022A of the legs 1021 and 1022 are radially remote from the axis X-X by a value denoted Δ in FIG. 25, which is larger than the outer radius $r_{1011}$ of the skirt 1011 of the element 1010. Thus, in this configuration of the suture members 1020, the legs 1021 and 1022 of each of said members are ready to be fixedly connected to each other by an attached part 1024 belonging to the member 1020, said part 1024 being the fourth of the distinct parts making up each member 1020, which were mentioned above. These attached parts 1024 are also in place in FIG. 27, while one of them is shown in FIG. 18, separated from the rest of the suture member 1020. However, before attaching these parts 1024, one particularly advantageous optional aspect is implemented, as illustrated in FIG. 26. As clearly shown by comparing FIGS. 25 and 26, the legs 1021 and 1022 of each suture member 1020 are brought axially closer to each other, owing to the arrangements related to the slit 1023C, described above. In practice, as also mentioned relative to the first embodiment, it is preferably the latter 2 that is biased by the surgeon to bring the neck 2A thereof closer to the orifice 3A of the urethra 3, this approach being accompanied and/or commanded by the proximal shift of the end 1021B of the leg 1021 along the slit 1023C. Under the effect of the backstop notches 1023D, the relative approach of the legs 1021 and 1022 is in a single direction, in other words irreversible: it is therefore possible to say that the attached joining between the side of the neck 2A of the bladder and the side of the orifice 3A of the urethra 3 is tightened in the direction of the axis X-X, in other words in the longitudinal direction of the urethra.

Figure 27:
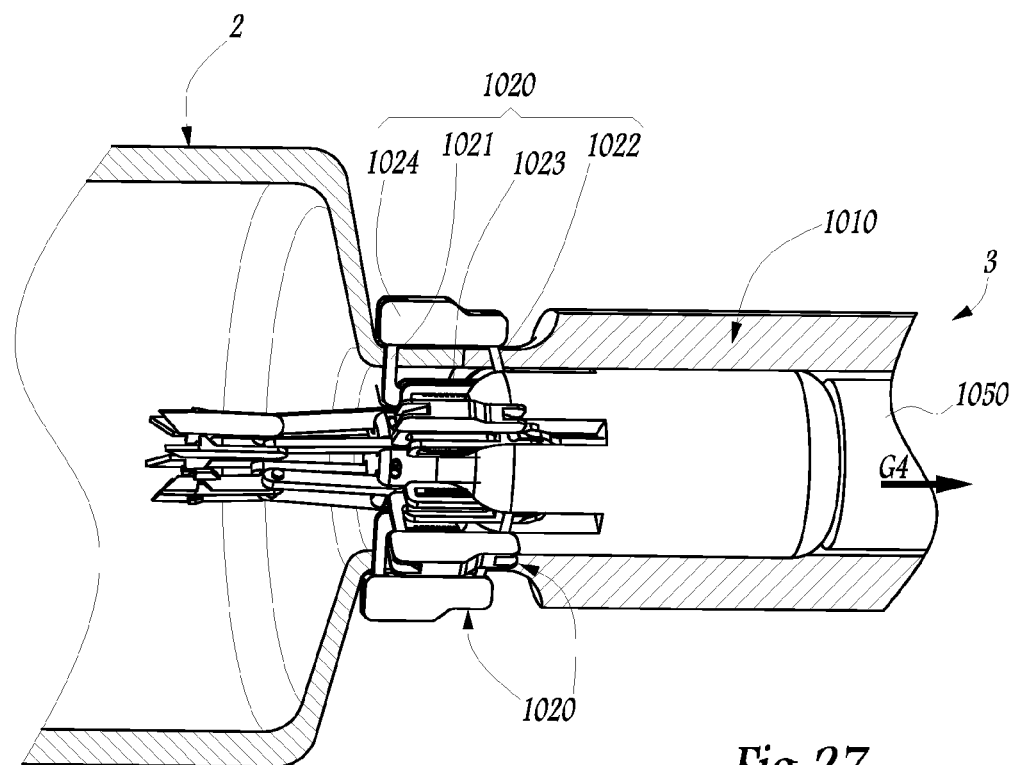

As briefly mentioned above, the following operating stage consists of attaching the parts 1024, as shown in FIG. 27. In practice, each attached part 1024 is capable of cooperating in a formfitting manner with both the free end 1021A of the corresponding leg 1021 and the free end 1022A of the corresponding leg 1022, so as to be fixedly attached to those ends 1021A and 1022A, the latter thus being fixedly attached to each other by the part 1024. Various embodiments can be considered for the parts 1024 inasmuch as those various embodiments make it possible to fixedly clip the ends 1021A and 1022A once those ends are in the deployed configuration of FIGS. 25 and 26. In this respect, the shoulders 1021E and 1022E of the ends 1021A and 1022A of the legs are advantageously used to cooperate in a formfitting manner with dedicated areas of the part 1024, so as to prevent disengagement of those ends once they are placed engaged with the part 1024.

Likewise, various operating techniques can be considered to place the parts 1024: these parts 1024 may be individually attached by hand by the surgeon, or may be supported by an ad hoc ancillary device, or may be supported by an ancillary device previously used during the surgical operation, in particular by the applicator 1040. Furthermore, the moment when the parts 1024 are placed may be different from that considered in light of FIG. 27: in fact, as one alternative not shown, it may be considered to attach the parts 1024 once the ends 1021A of the legs 1021 have passed through the wall of the bladder 2, in other words as of the step illustrated in FIG. 21, having understood that the ends 1022A of the legs 1022 are then only clipped to the parts 1024 already present once those ends 1022A have passed through the urethra 3, i.e., from the step illustrated in FIG. 25. In other words, in the extension of this operating alternative, the parts 1024 may advantageously be used to form respective abutments for the legs 1021 when the tip 1021B thereof perforate the wall of the bladder 2.

Figure 28:
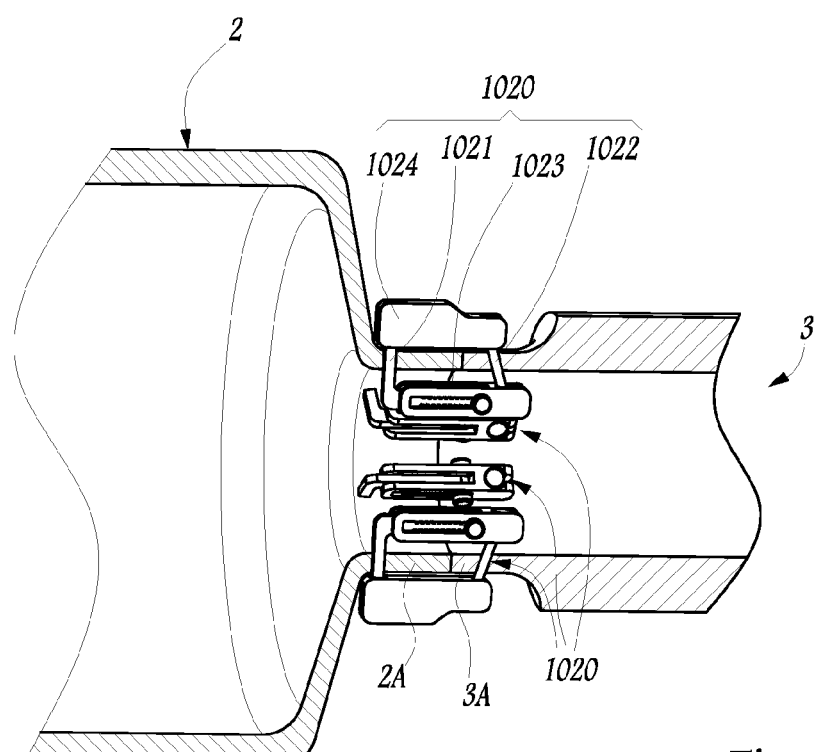

The surgeon must then finish releasing the suture members 1020 with respect to the element 1010. To that end, if applicable after having actuated a mechanical release command, in particular using the urethra probe 1050, the element 1010 being discharged by the inside of the urethra 3, by driving the urethra probe 1050, as indicated by arrow G4 in FIG. 27. The surgical operation is then complete, the suture members 1020 remaining in place in the deployed configuration, which is frozen by the attached parts 1024, each overlapping the anastomosis interface made between the neck 2A of the bladder 2 and the terminal orifice 3A of the urethra 3, as shown in FIG. 28.

Subsequently, the suture members 1020 will gradually be resorbed, after scarring of the anastomosis.

Thus, it is understood from the preceding description of the second embodiment, relative to FIGS. 16 to 28, that this second embodiment differs from the first embodiment by several aspects, i.e., inter alia, the following:

rather than being a single piece like the suture elements 20, the suture elements 1020 are each made up of four distinct parts 1021, 1022, 1023 and 1024, each suture member 1020 going, like each suture element 20, from an initial retracted configuration, in which the free ends 1021A and 1022A of the legs 1021 and 1022 are radially closer to the axis X-X than the outer surface of the element 1010 is, in particular for purposes of insertion without interference and placement of that element inside the bladder, to a deployed final configuration, in which the free ends 1021A and 1022A of the legs 1021 and 1022 are fixedly connected to each other by one of the attached parts 1024, the transition between those retracted and deployed configurations being done, as for the suture elements 20, subject to the at least local deformation and the displacement of the legs 1021 and 1022;

furthermore, owing to the production of the bridge 1023 in the form of a separate part, to which the legs 1021 and 1022 are movably assembled, the second embodiment allows significant tightening of the anastomosis, this tightening be also being able to be global or adaptive, i.e., in the latter case, the tightening stresses respectively applied to the suture members are specific to each member and may differ from one member to the next;

rather than having the entire member for biasing the suture members in displacement and deformation be commanded by the urethra probe, as is the case for the mechanism 30, the mechanism 1030 is partially controlled by the applicator 1040 and partially by the urethra probe 1050; one of the advantages related to this aspect is that the legs 1021 make it possible, while the element 1010 is still mechanically connected to the applicator 1040, to temporarily immobilize the element 1010 in the bladder 2 to be treated; in other words, in addition to performing the function of the legs 21, the legs 1021 at least partially perform the function allocated to the hooks 14; and as explained above, the mechanism 1030, in addition to a function similar to that of the mechanism 30, i.e., biasing the suture members in displacement and deformation, also performs a tubularization function with respect to the bladder 2, thereby making it possible to reconstruct the neck 2A of that bladder easily.

Of course, various arrangements and alternatives to the system described relative FIGS. 16 to 28, as well as the method for implementing that system, can also be considered.

In particular, alternatives to that system consist of having only some of the aspects that differ from the first embodiment be present.

Furthermore, considerations outside the specifications developed in this document are not limiting for this invention. As an example, the various components of the system, other than the bioresorbable suture members, are indifferently disposable or reusable.

Lastly, although the entire description above has been done in the context of performing an anastomosis between the bladder 2 and the urethra 3 of a patient, it will be understood that the system according to the invention, as well as the method for implementing that system, can more generally be applied to two hollow ducts of a patient that need to be connected by anastomosis. Thus, in addition to the example of the bladder and urethra, the aforementioned two hollow ducts may consist of intestinal, vascular, etc. ducts.

The invention claimed is:

1. A surgical treatment system for performing an anastomosis between two hollow ducts of a patient, said system comprising:
   at least one suture member, made from a bioresorbable material and including two legs, which have respective free ends suitable for being fixedly attached to each other by cooperating in a formfitting manner either with each other, or with an attached part of the suture member, and which, outside said free ends, are at least partially deformable,
   a support element, which is elongated along an axis of the support member and which is suitable both for movably supporting the at least one suture member and for being inserted along the direction of the axis into one of the two hollow ducts of the patient, and
   a mechanism for biasing the at least one suture member, which is movably supported by the support element being at least partially arranged in the support element, and which is suitable for displacing and deforming the at least one suture member between a retracted configuration, in which the respective free ends of the two legs of the at least one suture member are movable relative to one another, while each being arranged at a radial distance from the axis that is smaller than the outer radius of the support element, and a deployed configuration, in which the respective free ends of the two legs of the at least one suture member are arranged outside the support element to be fixedly attached to each other, while each being situated at a radial distance from the axis that is larger than the outer radius of the support member, after having transversely passed through respective walls of the two hollow ducts of the patient from the inside out.

2. The system according to claim 1, wherein the free end of at least one of the two legs of the at least one suture member has, opposite the rest of the leg, a tip, said tip having, in a connection area between the rest of the leg, a transverse section larger than that of the rest of the leg so as to form a transition shoulder that is capable of preventing the release of the free end of the leg with respect to the wall of the hollow ducts, as well as with respect to said attached part once the free end is engaged with said attached part.

3. The system according to claim 2, wherein the tip is capable of perforating the wall of the hollow ducts.

4. The system according to claim 1, wherein the mechanism is provided with first means for weakening or even perforating the wall of one of the hollow ducts in one or more portions designed to be passed through by the at least one suture member when the at least one goes from the retracted configuration to the deployed configuration.

5. The system according to claim 1, wherein the system further comprises an applicator for placing and attaching the support element in one of the hollow ducts.

6. The system according to claim 5, wherein the applicator is provided with second means for weakening or even perforating the wall of one of the hollow ducts in one or more portions designed to be passed through by the at least one suture member when the at least one goes from the retracted configuration to the deployed configuration.

7. The system according to claim 5, wherein the applicator has a distal end configured to cooperate with and thus command at least part of the mechanism.

8. The system according to claim 1, wherein the mechanism is suitable for displacing and deforming the at least one suture member between the retracted and deployed configurations by successively going through both of two intermediate configurations, i.e., a first intermediate configuration, in which a first of the two legs of the at least one suture member extends through the wall of one of the two hollow ducts of the patient, with the free end of the first leg situated outside that wall and not fixedly attached to the free end of the second leg, and a second intermediate configuration, in which the second leg extends through the wall of the other of the two hollow ducts, with the free end of the second leg situated outside the wall of the other of the two hollow ducts and not fixedly attached to the free end of the first leg.

9. The system according to claim 8, wherein the mechanism includes:
   a lifting strip which, relative to the support element, is translatably mounted along the axis and is capable of translating the at least one suture member to move the at least one suture member from the retracted configuration to the first intermediate configuration;
   a push-piece, which is translatably mounted along the axis relative to the lifting strip and which is suitable for deforming the second leg of the at least one suture member to move the at least one suture member from the first intermediate configuration to the second intermediate configuration, and
   a guide, which is fixedly attached to the support element along the axis and which, includes a separating portion inserted between the two legs of the at least one suture member and delimiting both a ramp surface for the first leg and a radial immobilization surface for the second leg such that, by translating the lifting strip, the free end of the first leg moves away, in a direction substantially radial to the axis, with respect to the free end of the second leg when the at least one suture member goes from the retracted configuration to the first intermediate configuration, then, by opposite translation of the push-piece, the free end of the second leg comes closer, along a direction substantially radial to the axis, with respect to the free end of the first leg when the at least one suture member goes from its first intermediate configuration to its second intermediate configuration.

10. The system according to claim 9, wherein the guide is rotatably mounted on the axis relative to the support element and is suitable, while the at least one suture member is in the second intermediate configuration, for being rotated around itself so as to release, along a direction orthoradial to the axis, the separating portion from between the two legs of the at least one suture member to move the at least one suture member into the deployed configuration.

11. The system according to claim 10, wherein, for the or each suture member, the separating portion of the guide is provided with a heel, which extends, along a direction peripheral to the axis, the radial immobilization surface for the second leg and which is connected to the ramp surface by a hollow shoulder in which the first leg is received by elastic return to mechanically engage the free end of the first leg with the free end of the second leg.

12. The system according to claim 9, wherein the lifting strip is rotatably mounted around the axis relative to the support element and is suitable, while the at least one suture member goes from the second intermediate configuration to the deployed configuration, for radially displacing, by cam effect, an opposed end of the first leg of the at least one suture member, opposite the free end of the first leg, radially toward the outside of the support element.

13. The system according to claim 8 wherein the mechanism includes:
    an arm that is tiltably mounted on the support element and along at least part of which the first leg of the at least one suture member extends such that the arm stresses and guides the displacement of said first leg to move the at least one suture member from its retracted configuration to the first intermediate configuration; and
    at least one push-piece, which is translatably mounted along the axis relative to the support element and which is suitable for acting on the second leg of the at least one suture member and stressing the second leg of the at least one suture member to deform relative to the rest of the at least one suture member so as to move each suture member from the first intermediate configuration to the second intermediate configuration.

14. The system according to claim 8, wherein the first leg of the at least one suture member extends along a part of the mechanism such that the first leg of the at least one suture member in the first intermediate configuration successively has a general U shape and a general L shape to tubularize the wall of the hollow duct through which the first leg extends.

15. The system according to claim 14 wherein the first leg of the at least one suture member extends along two segments included by the arm and which are articulated to each other, such that the first leg of the at least one suture member in the first intermediate configuration successively has a general U shape and a general L shape by relative tilting of the two segments.

16. The system according to claim 8, wherein the at least one suture member further includes a movable connecting bridge between the two legs, to which bridge the first leg of the at least one suture member is movably assembled, the first leg being moved relative to the bridge when the at least one suture member goes from the retracted configuration to the first intermediate configuration.

17. The system according to claim 8, wherein the at least one suture member further includes a movable connecting bridge between the two legs, to which bridge the second leg of the at least one suture member is movably assembled, the second leg being moved relative to the bridge when the at least one suture member goes from the first intermediate configuration to the second intermediate configuration.

18. The system according to claim 1, wherein the at least one suture member further includes a movable connecting bridge between the two legs, to which bridge at least one of the two legs is movably assembled.

19. The system according to claim 18, wherein the bridge is provided with approach means for axially moving the two legs of the at least one suture member closer together, said approach means being suitable, when the suture member is in the deployed configuration, to axially guide the two legs toward one another, at the location where the two legs cross the walls of the hollow ducts, while retaining the legs relative to one another to prevent them from separating axially, so as to tighten the anastomosis between the ducts.

20. The system according to claim 19, wherein said approach means is at the location where the two legs cross the walls of the hollow ducts.

21. The system according to claim 1, wherein the two legs of the at least one suture member are, opposite their free end, permanently connected to each other elastically deformably such that the suture member forms a suture element.

22. The system according to claim 21, wherein said suture element is in a single piece.

23. The system according to claim 1, wherein the support element is provided with immobilization means for removable immobilizing the support element in one of the hollow ducts.

24. The system according to claim 1, wherein the system further comprises an applicator for placing the support element in one of the hollow ducts and for controlling the immobilization means.

25. The system according to claim 1, wherein the system further comprises a probe for commanding the mechanism.

26. The system according to claim 14, wherein the probe is suitable for being inserted into one of the hollow ducts, and has a distal end configured to cooperate with and thus command at least part of the mechanism.

27. A surgical treatment method for performing an anastomosis between two hollow ducts of a patient wherein:
    at least one suture member is provided, the at least one suture member being made from a bioresorbable material and including two legs that have respective free ends suitable for being fixedly attached to each other by cooperating in a formfitting manner either to each other, or to an attached part of the suture member,
    a support element is further provided, the support member being elongated along an axis of the support member and movably supporting the at least one suture member,
    the support element is inserted into one of the two hollow ducts of the patient along the direction of the axis, while the at least one suture member is in a retracted configuration, in which the free ends of the two legs of the suture member are movable relative to one another, while each being arranged at a radial distance from the axis that is smaller than the outer radius of the support element, and
    the at least one suture member is mechanically biased so as to displace and deform the at least one suture member from the retracted configuration to a deployed configuration, in which the respective free ends of the two legs of the at least one suture member are arranged at the outside of the support element to be fixedly attached to each other, while each being situated at a radial distance from the axis that is larger than the outer radius of the support element, after said free ends have transversely passed through respective walls of the two hollow ducts of the patient from the inside out.

28. The method according to claim 27, wherein the two hollow ducts are the bladder and urethra of the patient.

29. The method according to claim 28, wherein the method is performed after a prostatectomy.

30. The method according to claim 28, wherein a probe for controlling deployment of the at least one suture member is inserted into the urethra from the meatus to the terminal orifice of the urethra.

* * * * *